(12) United States Patent  
Laramy et al.

(10) Patent No.: US 9,700,244 B2  
(45) Date of Patent: Jul. 11, 2017

(54) WIRELESS DEGRADATION DATA GENERATOR FOR USE WITH A THERAPEUTIC SCAFFOLD AND METHODS FOR USE THEREWITH

(71) Applicant: Memory Effect Medical, LLC, Austin, TX (US)

(72) Inventors: Christine Laramy, Austin, TX (US); Bruce Stuckman, Austin, TX (US)

(73) Assignee: MEMORY EFFECT MEDICAL, LLC, Austin, TX (US)

(*) Notice: Subject to any disclaimer, the term of this patent is extended or adjusted under 35 U.S.C. 154(b) by 442 days.

(21) Appl. No.: 14/159,157

(22) Filed: Jan. 20, 2014

(65) Prior Publication Data

US 2014/0206958 A1    Jul. 24, 2014

Related U.S. Application Data

(63) Continuation-in-part of application No. 13/956,501, filed on Aug. 1, 2013.

(Continued)

(51) Int. Cl.
*A61F 2/06* (2013.01)
*A61B 5/145* (2006.01)
*A61F 2/82* (2013.01)
*A61F 2/95* (2013.01)
*A61B 17/12* (2006.01)
*A61B 17/00* (2006.01)

(52) U.S. Cl.
CPC .... *A61B 5/14503* (2013.01); *A61B 17/12113* (2013.01); *A61B 17/12145* (2013.01); *A61F 2/82* (2013.01); *A61F 2/95* (2013.01); *A61B 17/12177* (2013.01); *A61B 2017/0003* (2013.01); *A61B 2017/00026* (2013.01); *A61B 2017/00221* (2013.01); *A61B 2017/00867* (2013.01); *A61B 2017/12054* (2013.01)

(58) Field of Classification Search
CPC ........ A61B 17/12145; A61B 17/12113; A61B 5/14503; A61B 5/6652; A61B 5/6862; A61F 2/95; A61F 2/82; A61F 2/0077; A61L 27/52; A61L 27/38; A61L 27/46; A61L 27/48; A61L 27/58; A61L 27/60
See application file for complete search history.

(56) References Cited

U.S. PATENT DOCUMENTS 4,026,276 A * 5/1977 Chubbuck ............ A61B 5/0031  
600/407  
7,612,325 B1 * 11/2009 Watkins, Jr. ........... G01N 27/12  
250/221

(Continued)

*Primary Examiner* — Tuan V Nguyen  
(74) *Attorney, Agent, or Firm* — Garlick & Markison; Bruce E. Stuckman

(57) ABSTRACT

A degradation data generator is used with a scaffold for delivery within a patient. The degradation data generator includes a driving circuit electrically coupled to drive an impedance of the scaffold. A detection circuit generates degradation data based on the impedance of the scaffold or other properties such as RF or lightwave transmission, conductance or absorption. The degradation data indicates an amount of biodegradation of the scaffold. A wireless transmitter is coupled to transmit the degradation data to a wireless degradation data receiver, while the scaffold is within the patient.

11 Claims, 29 Drawing Sheets

Related U.S. Application Data

(60) Provisional application No. 61/885,886, filed on Oct. 2, 2013, provisional application No. 61/892,901, filed on Oct. 18, 2013, provisional application No. 61/754,473, filed on Jan. 18, 2013.

(56) References Cited

U.S. PATENT DOCUMENTS

| | | | |
|---|---|---|---|
| 8,750,983 B2* | 6/2014 | Bonutti | A61N 7/00 604/20 |
| 2005/0267570 A1* | 12/2005 | Shadduck | A61B 17/12022 623/1.44 |
| 2006/0064082 A1* | 3/2006 | Bonutti | A61N 7/00 606/32 |
| 2006/0226575 A1* | 10/2006 | Maghribi | B29C 41/003 264/293 |
| 2008/0281400 A1* | 11/2008 | Philipp | A61F 2/86 623/1.15 |
| 2011/0213221 A1* | 9/2011 | Roche | A61B 5/0031 600/301 |

* cited by examiner

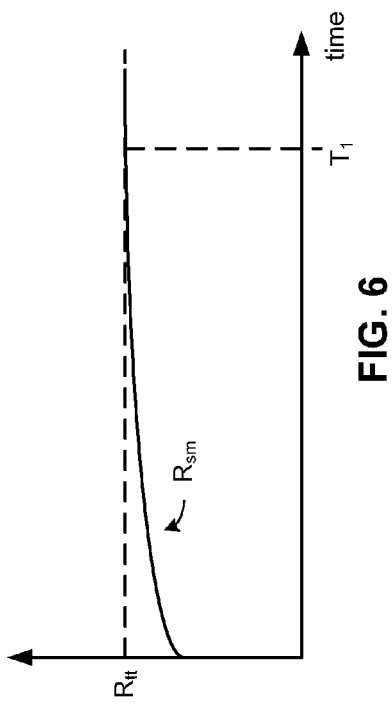
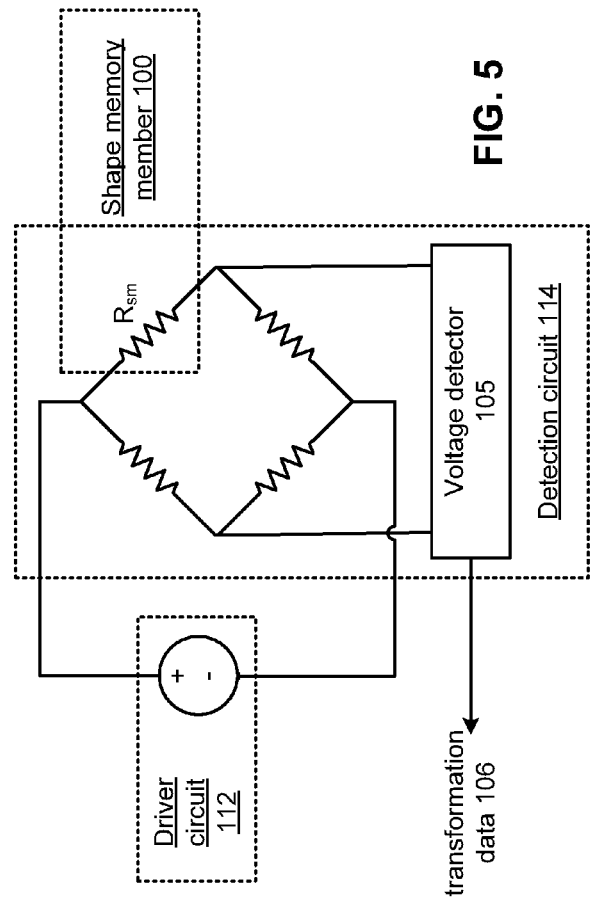
FIG. 6
FIG. 5

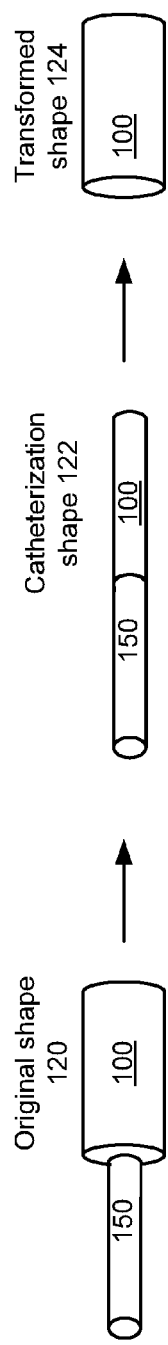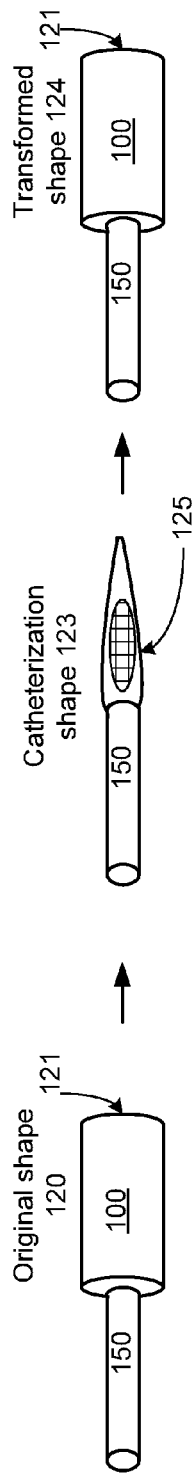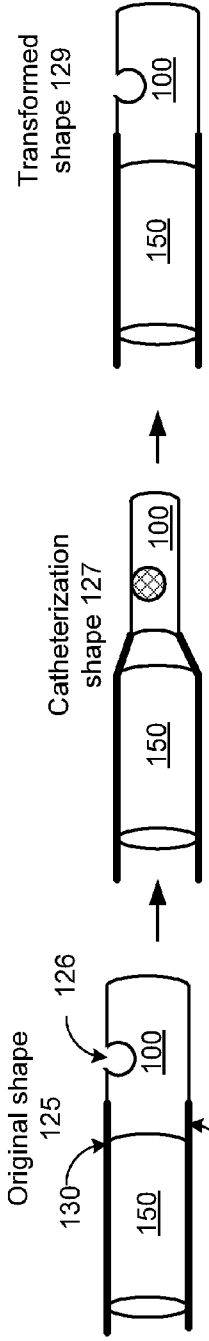

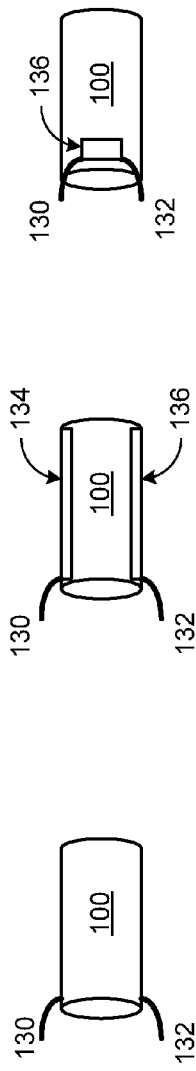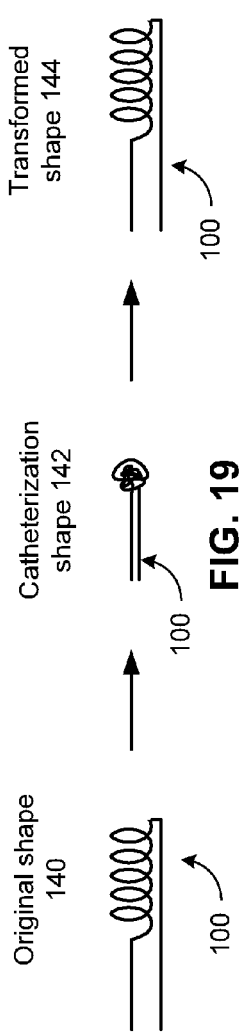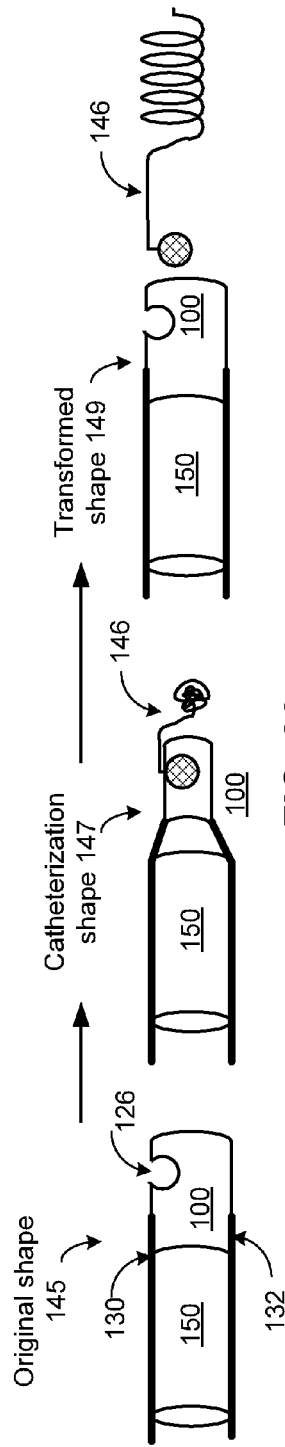

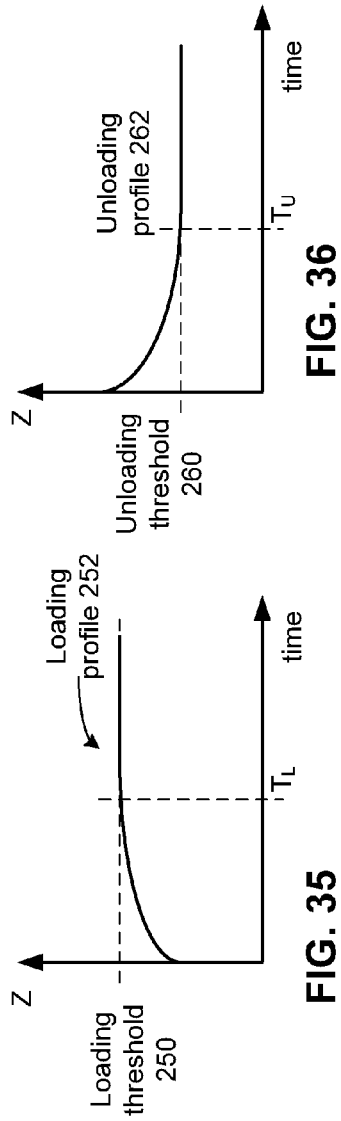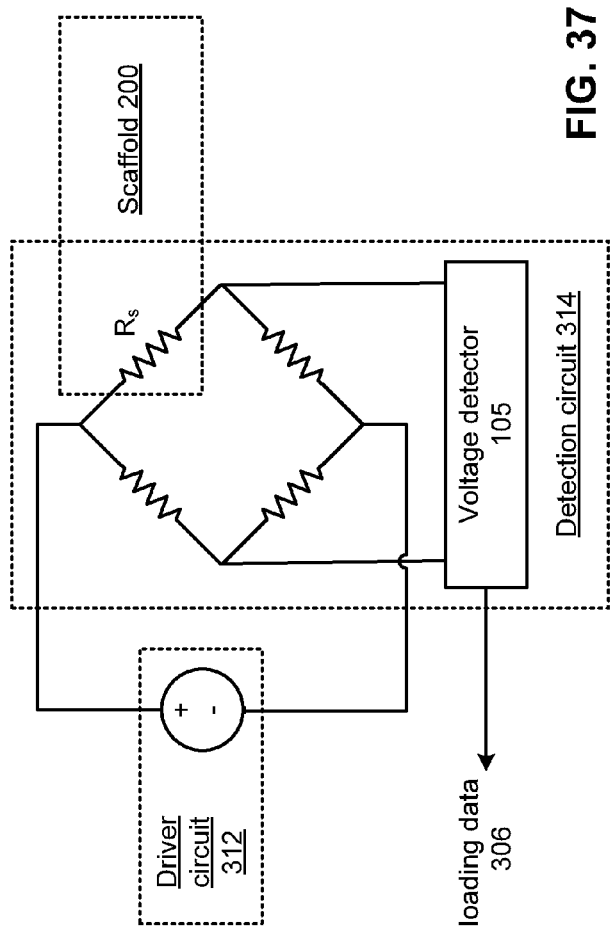

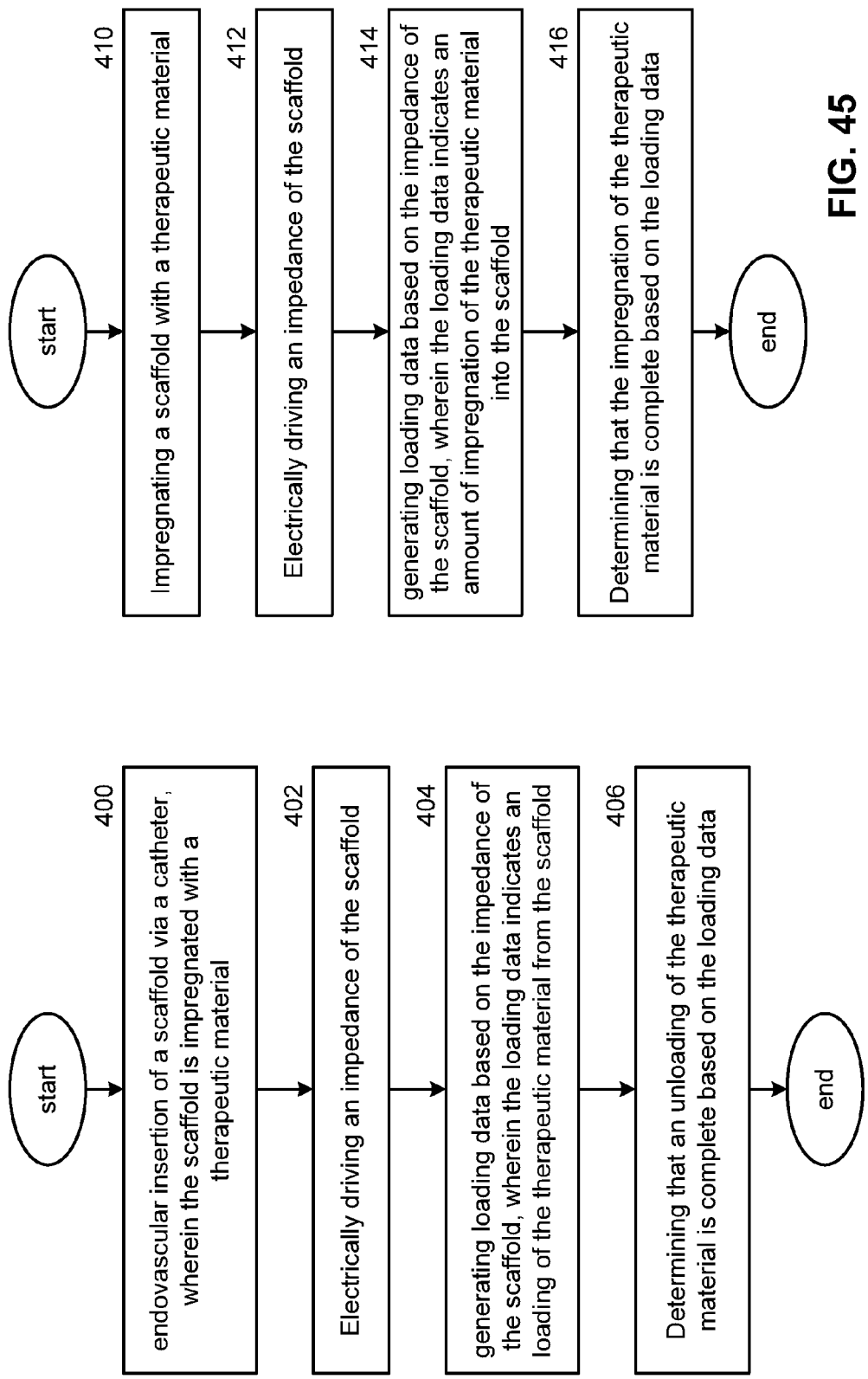

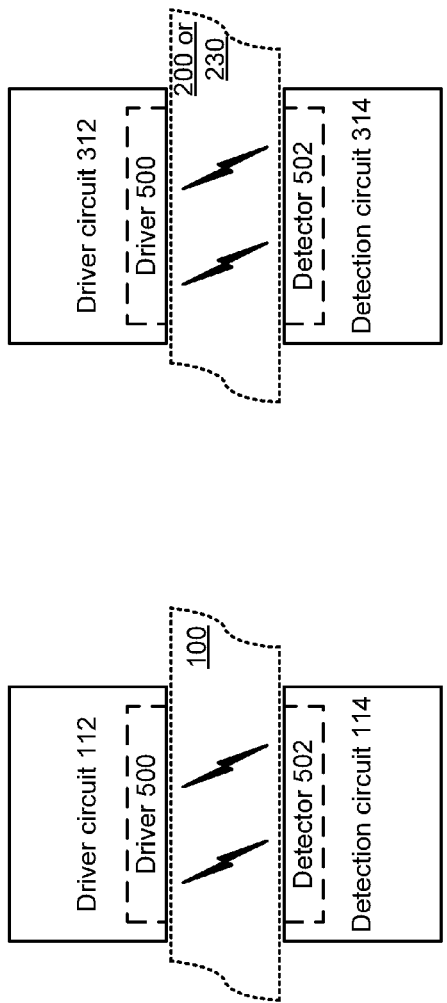
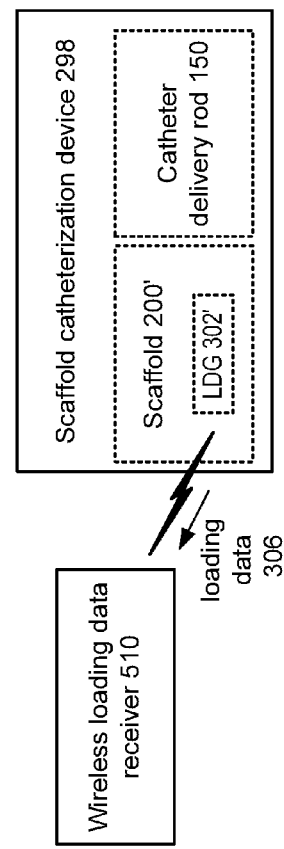
FIG. 46
FIG. 47
FIG. 48

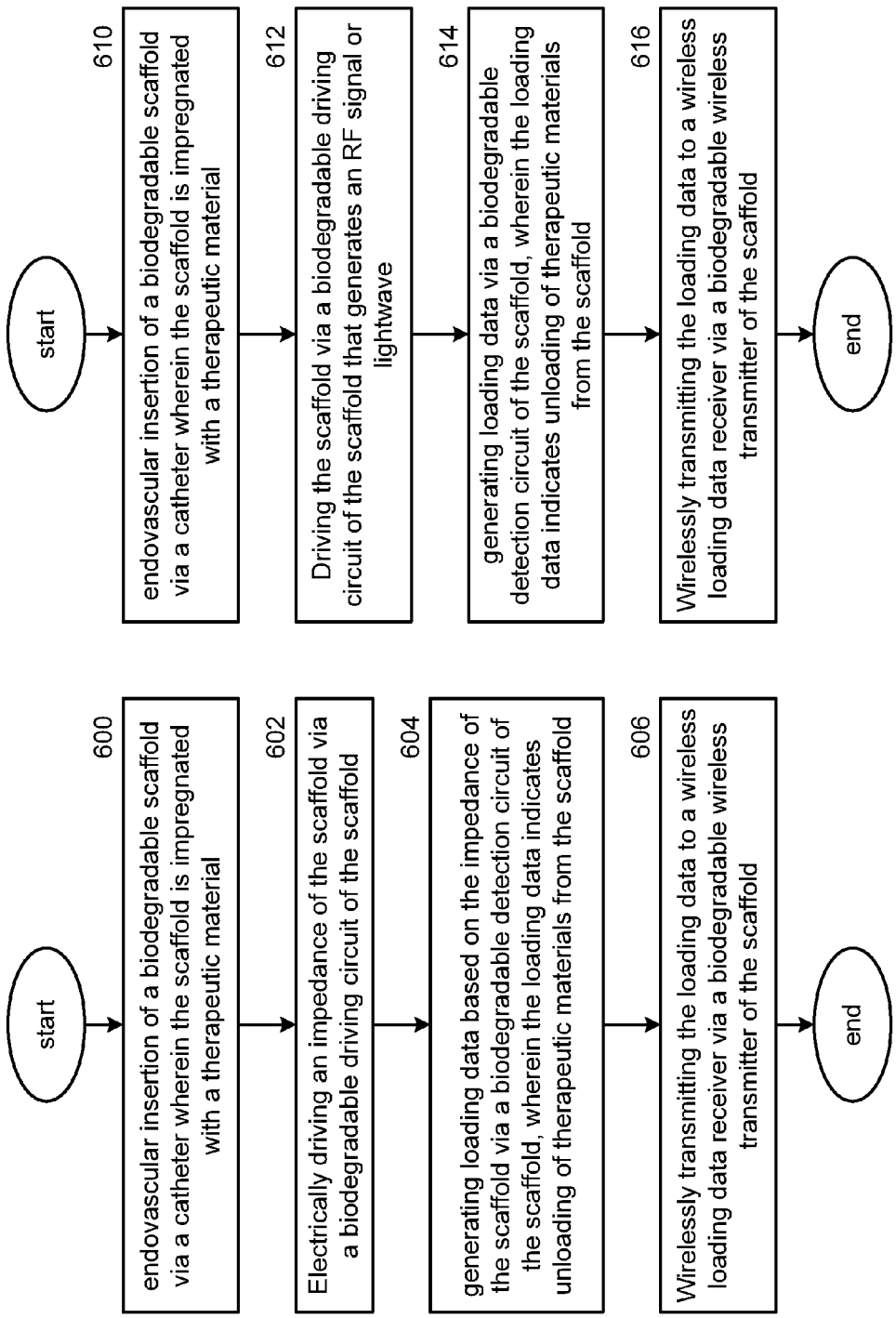

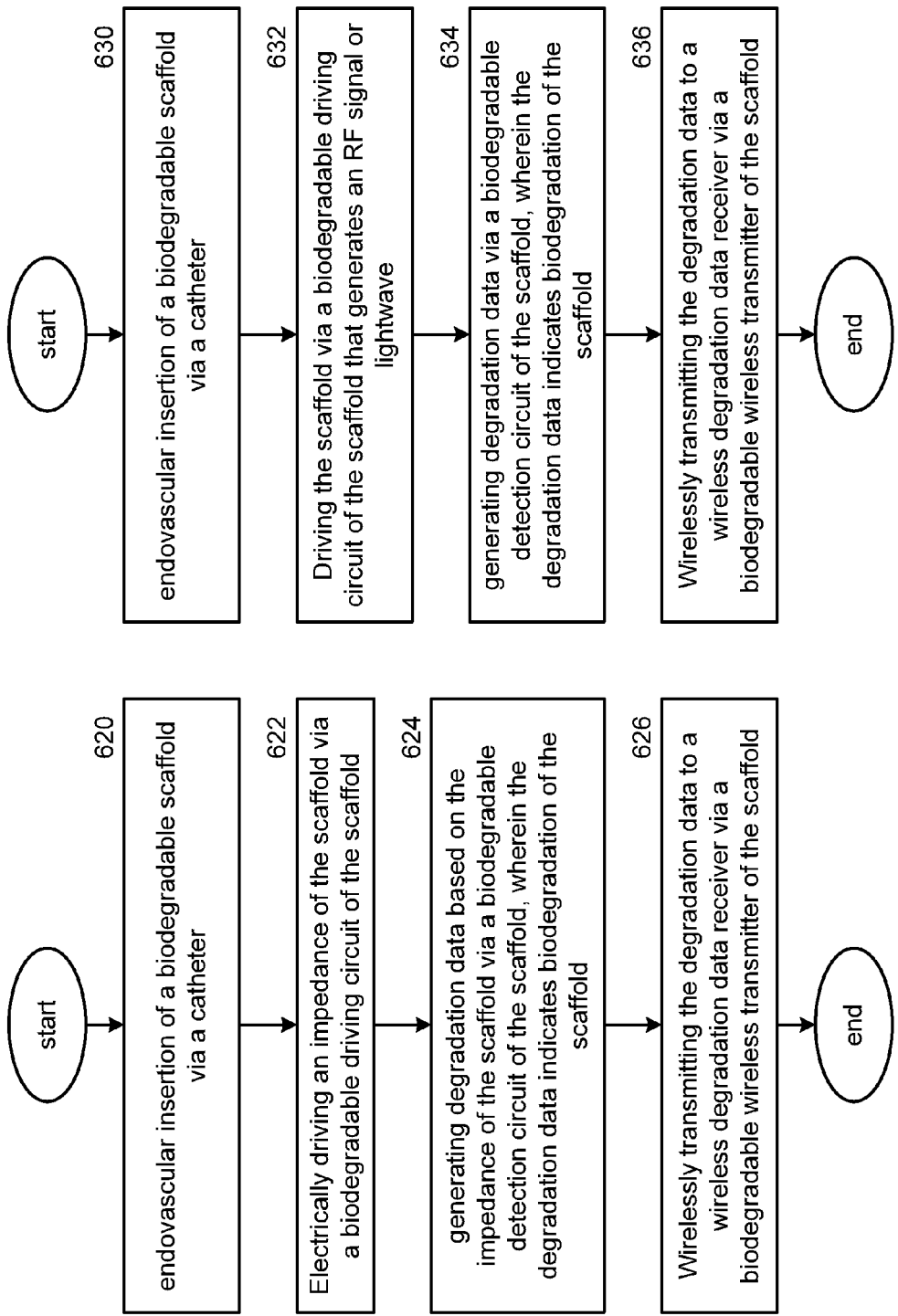

WIRELESS DEGRADATION DATA GENERATOR FOR USE WITH A THERAPEUTIC SCAFFOLD AND METHODS FOR USE THEREWITH

CROSS REFERENCE TO RELATED PATENTS

The present U.S. Utility patent application claims priority pursuant to 35 U.S.C. §119(e) to U.S. Provisional Application No. 61/892,901, entitled "WIRELESS DEGRADATION DATA GENERATOR FOR USE WITH A THERAPEUTIC SCAFFOLD AND METHODS FOR USE THEREWITH", filed Oct. 18, 2013; and U.S. Provisional Application No. 61/885,886, entitled "SHAPE MEMORY CATHETERIZATION DEVICE WITH ELECTRICAL TRANSFORMATION FEEDBACK AND METHODS FOR USE THEREWITH", filed Oct. 2, 2013, both of which are hereby incorporated herein by reference in their entirety and made part of the present U.S. Utility patent application for all purposes.

The present U.S. Utility patent application claims priority pursuant to 35 U.S.C. §120 as a continuation-in-part of U.S. Utility application Ser. No. 13/956,501, entitled "SYSTEM FOR DEPLOYING A RESISTIVE SHAPE MEMORY CATHETERIZATION DEVICE AND METHODS FOR USE THEREWITH", filed Aug. 1, 2013, which claims priority pursuant to 35 U.S.C. §119(e) to U.S. Provisional Application No. 61/754,473, entitled "SHAPE MEMORY CATHETERIZATION DEVICE WITH ELECTRICAL TRANSFORMATION FEEDBACK AND METHODS FOR USE THEREWITH", filed Jan. 18, 2013, both of which are hereby incorporated herein by reference in their entirety and made part of the present U.S. Utility patent application for all purposes.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to medical devices that prepare and intravenously insert scaffolds in a patient to deliver therapeutic materials.

Description of Related Art

A wide range of medical treatments can be performed with a catheter that is intravenously inserted in a patient. Such catheterizations have reduced invasiveness compared with conventional treatments leading to lower risk to the patient, faster healing times, etc. Shape memory devices that change shape based on temperature have been used in such catheterizations. These devices can be lightweight and biocompatible.

The disadvantages of conventional approaches will be evident to one skilled in the art when presented the disclosure that follows.

BRIEF DESCRIPTION OF THE SEVERAL VIEWS OF THE DRAWING(S)

FIG. 5 is a schematic block diagram of an embodiment of a driver circuit 112 and detection circuit 114 in accordance with the present invention;

FIG. 6 is a graphical representation of a resistance profile in accordance with an embodiment the present invention;

FIG. 13 is a pictorial representation of the shape transformation of a shape memory member of in accordance with an embodiment the present invention;

FIG. 14 is a pictorial representation of the transformation of a shape memory member of in accordance with an embodiment the present invention;

FIG. 15 is a pictorial representation of the transformation of a shape memory member of in accordance with an embodiment the present invention;

FIG. 16 is a pictorial representation of the transformation of a shape memory member of in accordance with an embodiment the present invention;

FIG. 17 is a pictorial representation of the transformation of a shape memory member of in accordance with an embodiment the present invention;

FIG. 18 is a pictorial representation of the transformation of a shape memory member of in accordance with an embodiment the present invention;

FIG. 19 is a pictorial representation of the transformation of a shape memory member of in accordance with an embodiment the present invention;

FIG. 20 is a pictorial representation of the transformation of a shape memory member of in accordance with an embodiment the present invention;

FIG. 35 is a graphical representation of a loading profile in accordance with an embodiment the present invention;

FIG. 36 is a graphical representation of an unloading profile in accordance with an embodiment the present invention;

FIG. 37 is a schematic block diagram of an embodiment of a loading data generator in accordance with the present invention;

FIG. 44 is a flowchart representation of an embodiment of a method in accordance with the present invention;

FIG. 45 is a flowchart representation of an embodiment of a method in accordance with the present invention;

FIG. 46 is a schematic block diagram of an embodiment of driver circuit and detection circuit in accordance with the present invention;

FIG. 47 is a schematic block diagram of an embodiment of driver circuit and detection circuit in accordance with the present invention;

FIG. 48 is a schematic block diagram of an embodiment of a system for monitoring a scaffold in accordance with the present invention;

FIG. 56 is a flowchart representation of an embodiment of a method in accordance with the present invention;

FIG. 57 is a flowchart representation of an embodiment of a method in accordance with the present invention;

FIG. 58 is a flowchart representation of an embodiment of a method in accordance with the present invention; and FIG. 59 is a flowchart representation of an embodiment of a method in accordance with the present invention.

DETAILED DESCRIPTION OF THE INVENTION

Figure 1:
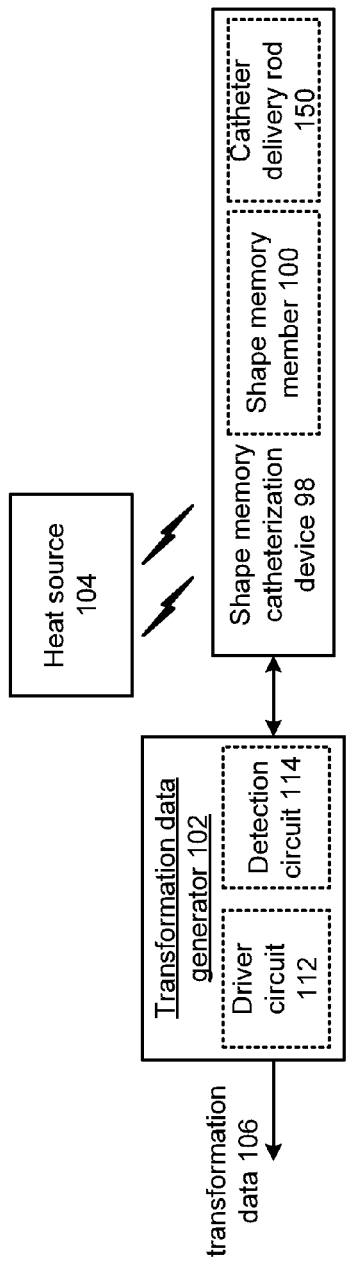
FIG. 1 is a schematic block diagram of an embodiment of a system for deploying a shape memory catheterization device 98 in accordance with the present invention.

FIG. 1 is a schematic block diagram of an embodiment of a system for deploying a shape memory catheterization device 98 in accordance with the present invention. In particular, a shape memory catheterization device 98 includes a catheter having a delivery rod 150 for use in conjunction with a catheterization procedure involving the insertion of the shape memory catheterization device 98 into a patient. Examples of such catheterization procedures include the insertion of an endovascular stent as part of an angioplasty or treatment of an aneurism or the intravenous deployment of another medical device, an intravenous drug deployment or the administration of anesthetic medication into the epidural space, the subarachnoid space, or around a major nerve bundle such as the brachial plexus, the administration of anesthetic medication into the epidural space, the subarachnoid space, or around a major nerve bundle such as the brachial plexus, an in vitro fertilization or other medical treatment, a urinary catheterization, treatment of an abdominal abscess, a balloon septostomy, balloon sinuplasty, catheter ablation, an in vitro fertilization or other medical treatment.

The shape memory catheterization device 98 includes a shape memory member 100 having a transition temperature that is higher than a normal body temperature of the patient. When heat is applied by a heat source 104 the shape memory member 100 of shape memory catheterization device 98 is heated above the transition temperature causes the shape memory member 100 to undergo a shape transformation from a catheterization shape into a transformed shape that is useful in the particular treatment. The heat source 104 can be an infrared emitter, laser or other light source, a heating coil or other electrical heating source, a microwave source or other electromagnetic source, a radiation source or other heat source. While shown separately from the shape memory catheterization device 98, the heat source 104 can be integrated into the shape memory catheterization device 98.

A transformation data generator 102 includes a circuit driver 112 for driving a circuit that includes at least one electrical element of the shape memory member 100 via a signal line included in the delivery rod and a plurality of electrodes that couple to the shape memory device 100. The transformation data generator 102 also includes a detection circuit 114 for generating transformation data 106 based on feedback generated by the detection circuit 114. The transformation data 106 indicates a shape transformation of the shape memory member 100 of the shape memory catheterization 98 device from the catheterization shape to the transformed shape. In an embodiment of the present invention the transformation data 106 can be displayed or otherwise used to provide visual, audible or tactile feedback to the users of shape memory catheterization device 98 that the shape memory member 100 has reached its transformation shape.

Further examples including numerous optional functions and features of shape memory catheterization device 98 are discussed in conjunction with FIGS. 2-30 that follow.

Figure 2:
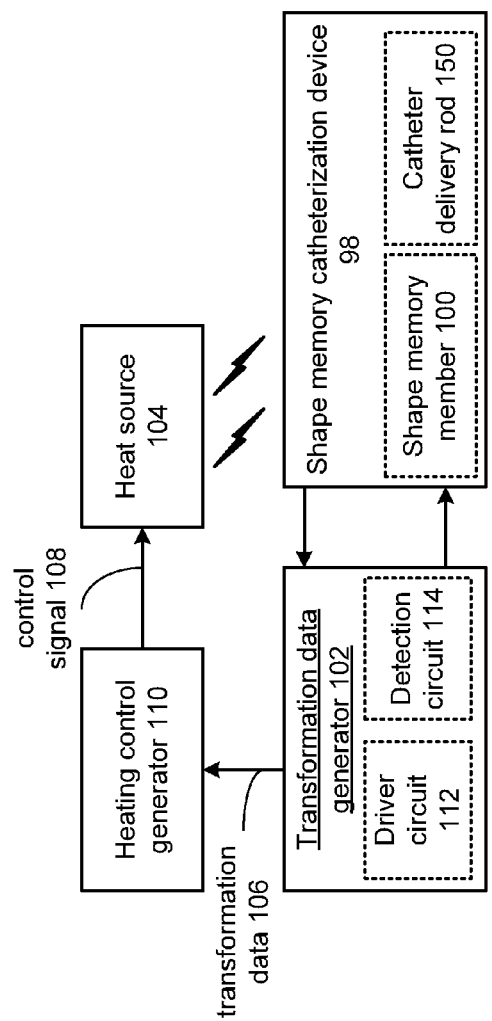
FIG. 2 is a schematic block diagram of an embodiment of a system for deploying a shape memory catheterization device 98 in accordance with the present invention.

FIG. 2 is a schematic block diagram of an embodiment of a system for deploying a shape memory catheterization device 98 in accordance with the present invention. In particular, a system is shown that includes many common elements of those described in conjunction with FIG. 1 that are referred to by common reference numerals. In addition, a heating control generator 110 is included that generates a control signal 108 for controlling the heat source 104 based on the transformation data 106. In operation, the heating control generator generates the control signal 108 to discontinue the heating of the shape memory catheterization device 98 when the transformation data 106 indicates the shape transformation of the shape memory member 100 from the catheterization shape to the transformed shape.

In an example of operation, the shape memory member 100 is a shape memory polymer, alloy or other device with a transition temperature that is slightly above the body temperature of the patient. The shape memory member 100 is heated above the transition temperature to effectuate the shape transformation of the shape memory member as part of the treatment. Overheating of blood or tissue can cause undesirable blood clotting during a treatment or other harmful effects. Discontinuing heating by heat source 104 after the shape transformation has occurred can avoid overheating the patient's tissue, blood and other body fluids during the procedure and allows the users of shape memory catheterization device to provide only as much heat as is reasonably necessary to effectuate the shape transformation.

Heating control generator 110 can be implemented using a processing device such as shared processing device, individual processing devices, or a plurality of processing devices and may further include memory. Such a processing device may be a microprocessor, micro-controller, digital signal processor, microcomputer, central processing unit, field programmable gate array, programmable logic device, state machine, logic circuitry, digital circuitry, and/or any device that manipulates signals based on operational instructions. The memory may be a single memory device or a plurality of memory devices. Such a memory device may be a read-only memory, random access memory, volatile memory, non-volatile memory, static memory, dynamic memory, flash memory, and/or any device that stores digital information. Note that when the processing device implements one or more of its functions via a state machine, digital circuitry, and/or logic circuitry, the memory storing the corresponding operational instructions is embedded with the circuitry comprising the state machine, digital circuitry, and/or logic circuitry.

Figure 3:
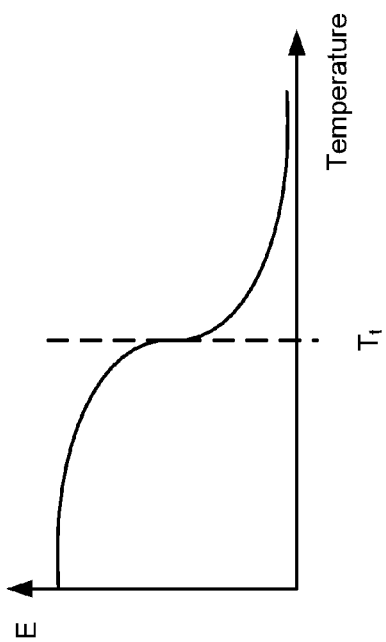
FIG. 3 is a graphical representation of a temperature profile of in accordance with an embodiment the present invention.

FIG. 3 is a graphical representation of a temperature profile in accordance with an embodiment of the present invention. In particular, a temperature profile is presented of a shape memory member, such as shape memory member 100. The shape memory member can be a shape memory polymer such as a cold hibernated elastic memory (CHEM) polymer or other shape memory polymer, shape memory alloy or other shape memory device. As shown, the elastic modulus, E, of the shape memory member 100 changes based on whether the temperature, T, of the shape memory member is above or below a transition temperature, $T_t$. For the range of temperatures $T<T_t$, the elastic modulus is high and the shape memory member is rigid and holds a particular shape. For the range of temperatures $T>T_t$, the elastic modulus is low and the shape memory member is flexible. Consider the example where the shape memory member 100 is a shape memory polymer that has a transition temperature, $T_t$, that corresponds to a glass transition. For the range of temperatures $T<T_t$, the shape memory member is in a glassy state and is rigid. For the range of temperatures $T>T_t$, the shape memory member is in a rubbery state and the shape memory member is flexible. This property of the shape memory member can be used to create a heat induced shape transformation as described in conjunction with FIG. 4.

Figure 4:
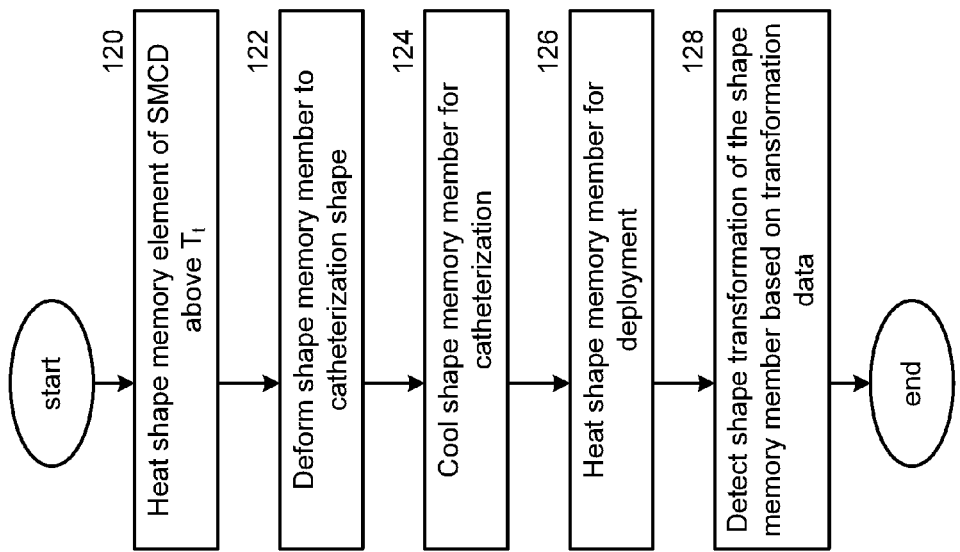
FIG. 4 is a flow diagram of an embodiment of a method in accordance with the present invention.

FIG. 4 is a flow diagram of an embodiment of a method in accordance with the present invention. In step 120, a shape memory member, such as shape memory member 100 of shape memory catheterization device 98, is heated above its transition temperature and enters a flexible state. In step 122, the shape memory member is deformed from an original shape into its catheterization shape. In step 124, the shape memory member is cooled while constrained to its catheterization shape, and becomes rigid, allowing it to retain its deformed catheterization shape when the constraint is removed. In step 126, the shape memory member is heated during catheterization for deployment as part of the catheterization treatment. When the shape memory member reenters the rubbery state, the shape memory member undergoes a shape transformation back to its original shape.

As shown in step 128, the shape transformation of the shape memory member 100 is detected based on transformation data, such as transformation data 106 generated by the transformation data generator 104. As discussed in conjunction with FIG. 1, the transformation data 106 can be displayed or otherwise used to provide visual, audible or tactile feedback to the users of shape memory catheterization device 98 that the shape memory member 100 has reached its transformation shape. As discussed in conjunction with FIG. 2, the transformation data can be used by a heating control generator to generate the control signal 108 to discontinue the heating of the shape memory member 100 when the transformation data indicates the shape transformation of the shape memory member has gone from the catheterization shape to the transformed shape. If the shape memory member 100 is a stent or other device that is to remain in the body, the cooling of the shape memory member back to the body temperature of the patient causes the shape memory member to return to its rigid state to hold the transformed shape.

In an embodiment, prior to step 120 a shape memory member can be formed into a desired deployment shape, such as via laser cutting or other cutting, by molding or by other formation technique. Prior to step 126, the shape memory member can be delivered via the catheter.

FIG. 5 is a schematic block diagram of an embodiment of a driver circuit 112 and detection circuit 114 in accordance with the present invention. In this embodiment, the shape memory member 100 includes a resistive element that has a resistance $R_{sm}$ that changes in response to the shape transformation of the shape memory member. For example, the shape memory member 100 can be a shape memory polymer with electrically resistive properties, that is surface doped with a conductive or partially conductive compound, or that is doped to saturation with a conductive or partially conductive compound. In a further example the shape memory member can be formed of a shape memory polymer to include a flexible resistive member such as a metallic foil element adhered or deposited on the surface of the shape memory member, a flexible foil or coil insert, a resistive foam member or insert or other resistive member. In addition, the shape memory member can be formed of a shape memory alloy that is electrically conductive with a resistance that changes in response to the shape transformation of the shape memory member 100.

The driver circuit includes a power source, such as the voltage source shown, that drives the detection circuit 114 and a wheatstone bridge formed with the resistive element of the shape memory member 100 and a plurality of fixed resistors. The voltage detector 105 monitors the change in resistance of the resistive element of shape memory member 100 and generates the transformation data 104, for example, when the change in resistance $R_{sm}$ indicates that the shape transformation has occurred.

In an embodiment, the voltage detector 105 generates the transformation data 106 to indicate the shape transformation of the shape memory member from the catheterization shape to the transformed shape when the resistance $R_{sm}$ of the resistive element compares favorably to a transformation threshold. In particular, the transformation data 106 can include a data flag having a first value that indicates the catheterization shape and a second value that indicates the transformed shape. The transition of the transformation data 106 from the first value to the second value can indicate that the transformation has occurred.

FIG. 6 is a graphical representation of a resistance profile of in accordance with an embodiment the present invention. An example resistance profile of a resistive element of shape memory member 100 is shown. As the shape memory member is heated in conjunction with the deployment of the shape memory catheterization device, the resistance, $R_{sm}$, changes with time. In particular, the resistance $R_{sm}$ changes in response to the shape transformation of the shape memory member 100 caused by the heating of the shape memory catheterization device.

As discussed in conjunction with FIG. 5, the voltage detector 105 generates the transformation data 106 to indicate the shape transformation of the shape memory member 100 from the catheterization shape to the transformed shape when the resistance $R_{sm}$ of the resistive element compares favorably to a transformation threshold. In the example shown, the transformation over time of the shape memory member causes the resistance $R_{sm}$ to increase. At a time, $T_1$, the resistance $R_{sm}$ reaches a transition threshold, $R_{tt}$, and stabilizes indicating the shape transformation is complete. In this example the voltage detector can include a comparator that generates the transformation data 106 when the $R_{sm}$ meets or exceeds the transition threshold, $R_{tt}$.

While the transformation over time of the shape memory member causes the resistance $R_{sm}$ to increase in the example shown, in other examples, the resistance may decrease depending on the nature of the original and catheterization shape of the shape memory member and/or the nature, position and orientation of the resistive element or elements included in the shape memory member 100, etc. Further, while the voltage detector has been described in terms of comparing the resistance $R_{sm}$ to a transition threshold, $R_{tt}$, other metrics such as the stabilization of the resistance $R_{sm}$ can likewise be employed.

Further, while the embodiments above contemplate a shape memory device 100 with a single resistive element, multiple resistive elements can be driven and monitored by transformation data generator 102. For example, resistive elements can be placed at multiple points, on multiple axes of transformation or otherwise on multiple portions of a shape memory member 100. In this configuration, transformation data 106 can be generated to indicate the transform shape when all of the resistive elements indicate a transformation has taken place.

Figure 7:
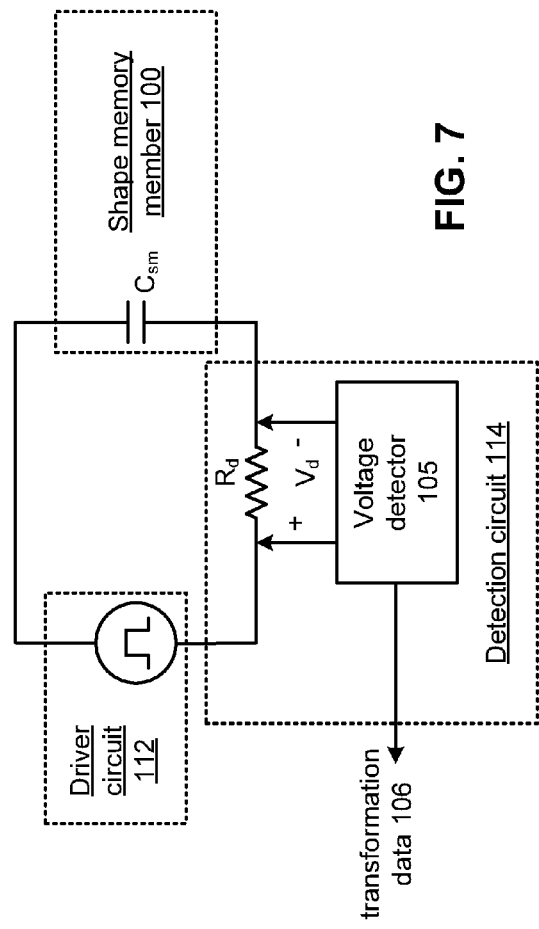
FIG. 7 is a schematic block diagram of an embodiment of a driver circuit 112 and detection circuit 114 in accordance with the present invention.

FIG. 7 is a schematic block diagram of an embodiment of a driver circuit 112 and detection circuit 114 in accordance with the present invention. In this embodiment, the shape memory member 100 includes a capacitive element that has a capacitance $C_{sm}$ that changes in response to the shape transformation of the shape memory member. For example, the shape memory member 100 can be a shape memory polymer with capacitive properties, that is includes a plurality of plates that are surface doped with a conductive or partially conductive compound, a metallic foil element adhered or deposited on the surface of the shape memory member or a conductive foam or other conductive element that forms the plates. The shape memory polymer further includes an electrolytic, dielectric or insulator made of a shape memory polymer that is disposed between the plurality of plates. In addition, the shape memory member can be formed of a shape memory alloy that is electrically conductive with a capacitance such as a parasitic capacitance that changes in response to the shape transformation of the shape memory member 100.

The driver circuit 112 includes a power source, such as the voltage source shown, that drives the detection circuit 114 via an alternating current such as the step waveform generator that is shown. The driver circuit further includes a detection resistance $R_d$ that forms an RC circuit with the capacitive element of the shape memory member 100. The voltage detector 105 monitors the change in capacitance of the capacitive element of shape memory member 100 based on monitoring the time of charging and/or discharging of the capacitive element. The voltage detector generates the transformation data 104, for example, when the change in capacitance $C_{sm}$ indicates that the shape transformation has occurred.

In an embodiment, the voltage detector 105 generates the transformation data 106 to indicate the shape transformation of the shape memory member from the catheterization shape to the transformed shape when the capacitance $C_{sm}$ of the capacitive element compares favorably to a transformation threshold. In particular, the transformation data 106 can include a data flag having a first value that indicates the catheterization shape and a second value that indicates the transformed shape. The transition of the transformation data 106 from the first value to the second value can indicate that the transformation has occurred.

Figure 8:
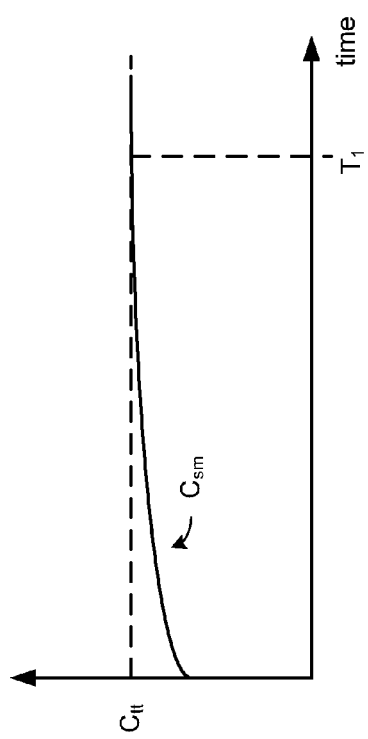
FIG. 8 is a graphical representation of a capacitance profile in accordance with an embodiment the present invention.

FIG. 8 is a graphical representation of a capacitance profile of in accordance with an embodiment the present invention. An example capacitance profile of a capacitive element of shape memory member 100 is shown. As the shape memory member 100 is heated in conjunction with the deployment of the shape memory catheterization device, the capacitance, $C_{sm}$, changes with time. In particular, the capacitance $C_{sm}$ changes in response to the shape transformation of the shape memory member caused by the heating of the shape memory catheterization device.

As discussed in conjunction with FIG. 7, the voltage detector 105 generates the transformation data 106 to indicate the shape transformation of the shape memory member from the catheterization shape to the transformed shape when the capacitance $C_{sm}$ of the capacitive element compares favorably to a transformation threshold. In the example shown, the transformation over time of the shape memory member causes the capacitance $C_{sm}$ to increase. At a time, $T_1$, the capacitance $C_{sm}$ reaches a transition threshold, $C_{tt}$, and stabilizes indicating the shape transformation is complete. In this example the voltage detector can include a comparator that generates the transformation data 106 when the $C_{sm}$ meets or exceeds the transition threshold, $C_{tt}$.

While the transformation over time of the shape memory member causes the capacitance $C_{sm}$ to increase in the example shown, in other examples, the capacitance may decrease depending on the nature of the original and catheterization shape of the shape memory member and/or the nature, position and orientation of the capacitive element or elements included in the shape memory member, etc. Further, while the voltage detector has been described in terms of comparing the capacitance $C_{sm}$ to a transition threshold, $C_{tt}$, other metrics such as the stabilization of the capacitance $C_{sm}$ can likewise be employed.

Further, while the embodiments above contemplate a shape memory device with a single capacitive element, multiple capacitive elements can be driven and monitored by transformation data generator 102. For example, capacitive elements can be placed at multiple points, on multiple axes of transformation or otherwise on multiple portions of a shape memory member 100. In this configuration, transformation data 106 can be generated to indicate the transformation shape when all of the capacitive elements indicate a transformation has taken place.

Figure 9:
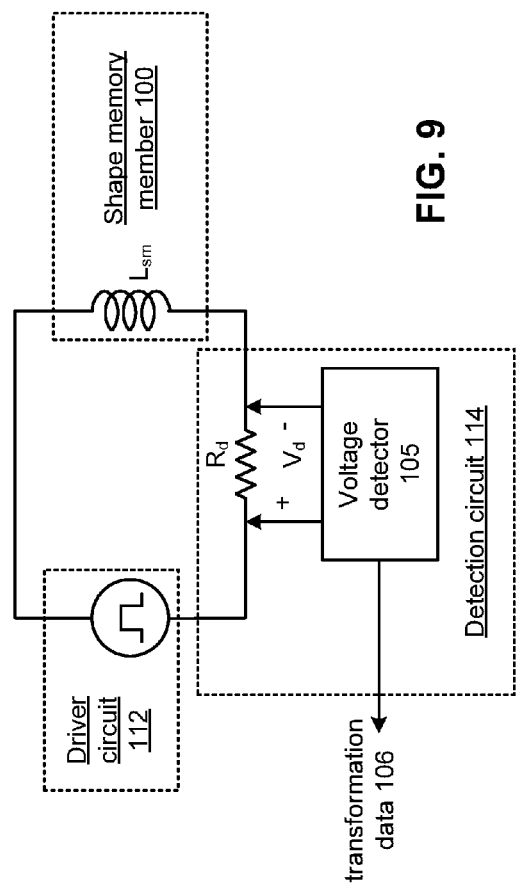
FIG. 9 is a schematic block diagram of an embodiment of a driver circuit 112 and detection circuit 114 in accordance with the present invention.

FIG. 9 is a schematic block diagram of an embodiment of a driver circuit 112 and detection circuit 114 in accordance with the present invention. In this embodiment, the shape memory member 100 includes an inductive element that has an inductance $L_{sm}$ that changes in response to the shape transformation of the shape memory member. For example, the shape memory member can be a shape memory polymer with electrically inductive properties, that is surface doped with a conductive or partially conductive compound, or that is doped to saturation with a conductive or partially conductive compound. In a further example the shape memory member can be formed of a shape memory polymer to include a flexible inductive member such as a metallic foil element adhered or deposited on the surface of the shape memory member, a flexible foil or coil insert, a conductive foam member or insert or other inductive member. In addition, the shape memory member can be formed of a shape memory alloy that is electrically conductive with an inductance that changes in response to the shape transformation of the shape memory member 100.

The driver circuit 112 includes a power source, such as the voltage source shown, that drives the detection circuit 114 via an alternating current such as the step waveform generator that is shown. The driver circuit further includes a detection resistance $R_d$ that forms an RL circuit with the inductive element of the shape memory member 100. The voltage detector 105 monitors the change in inductance of the inductive element of shape memory member 100 based on monitoring the time of charging and/or discharging of the inductive element. The voltage detector generates the transformation data 104, for example, when the change in inductance $L_{sm}$ indicates that the shape transformation has occurred.

In an embodiment, the voltage detector 105 generates the transformation data 106 to indicate the shape transformation of the shape memory member from the catheterization shape to the transformed shape when the inductance $L_{sm}$ of the inductive element compares favorably to a transformation threshold. In particular, the transformation data 106 can include a data flag having a first value that indicates the catheterization shape and a second value that indicates the transformed shape. The transition of the transformation data from the first value to the second value can indicate that the transformation has occurred.

Figure 10:
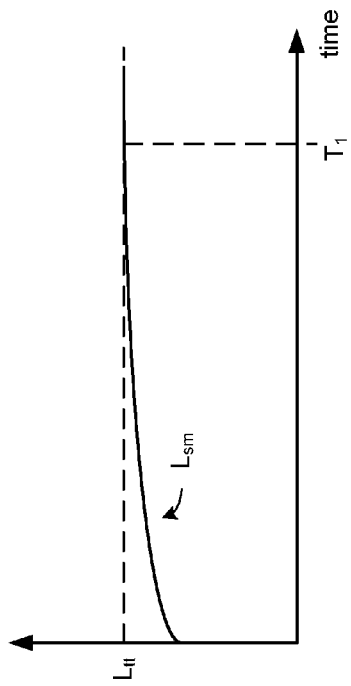
FIG. 10 is a graphical representation of inductance profile in accordance with an embodiment the present invention.

FIG. 10 is a graphical representation of an inductance profile of in accordance with an embodiment the present invention. An example inductance profile of an inductive element of shape memory member 100 is shown. As the shape memory member is heated in conjunction with the deployment of the shape memory catheterization device, the inductance, $L_{sm}$, changes with time. In particular, the inductance $L_{sm}$ changes in response to the shape transformation of the shape memory member caused by the heating of the shape memory catheterization device.

As discussed in conjunction with FIG. 9, the voltage detector 105 generates the transformation data 106 to indicate the shape transformation of the shape memory member from the catheterization shape to the transformed shape when the inductance $L_{sm}$ of the inductive element compares favorably to a transformation threshold. In the example shown, the transformation over time of the shape memory member causes the inductance $L_{sm}$ to increase. At a time, $T_1$, the inductance $L_{sm}$ reaches a transition threshold, $L_{tt}$, and stabilizes indicating the shape transformation is complete. In this example the voltage detector can include a comparator that generates the transformation data 106 when the inductance $L_{sm}$ meets or exceeds the transition threshold, $L_{tt}$.

While the transformation over time of the shape memory member causes the inductance $L_{sm}$ to increase in the example shown, in other examples, the inductance may decrease depending on the nature of the original and catheterization shape of the shape memory member and/or the nature, position and orientation of the inductive element or elements included in the shape memory member, etc. Further, while the voltage detector has been described in terms of comparing the inductance $L_{sm}$ to a transition threshold, $L_{tt}$, other metrics such as the stabilization of the inductance $L_{sm}$ can likewise be employed.

Further, while the embodiments above contemplate a shape memory device with a single inductive element, multiple inductive elements can be driven and monitored by transformation data generator 102. For example inductive elements can be placed at multiple points, on multiple axes of transformation or otherwise on multiple portions of a shape memory member 100. In this configuration, transformation data 106 can be generated to indicate the transform shape when all of the inductive elements indicate a transformation has taken place.

Figure 11:
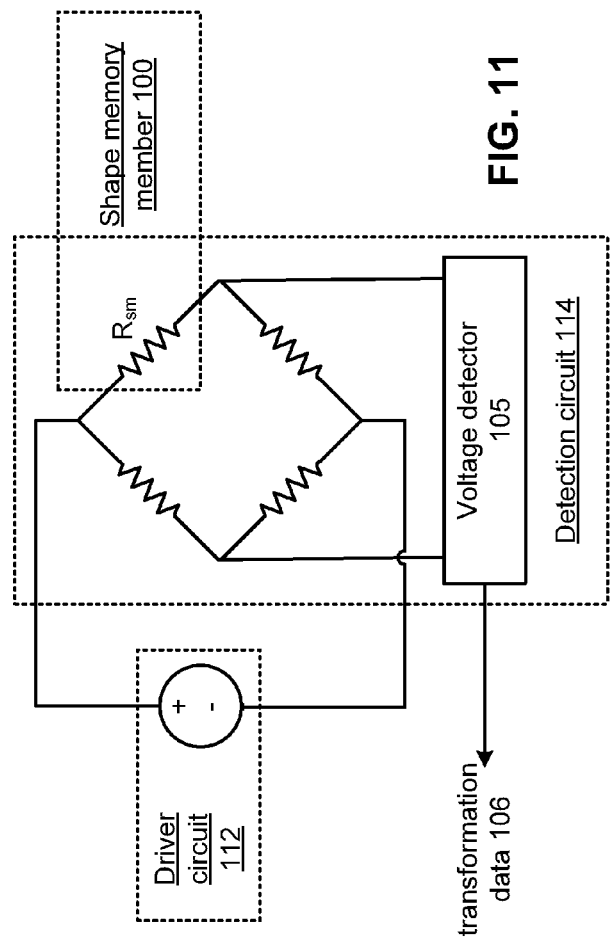
FIG. 11 is a schematic block diagram of an embodiment of a driver circuit 112 and detection circuit 114 in accordance with the present invention.

FIG. 11 is a schematic block diagram of an embodiment of a driver circuit 112 and detection circuit 114 in accordance with the present invention. In this embodiment, the shape memory member 100 includes a strain gage that has a resistance $R_{sm}$ that changes in response to the strain on the shape memory member 100. For example, the shape memory member 100 can be a shape memory polymer or other shape memory member with a strain gage adhered or deposited on the surface of the shape memory member. In particular, strain and corresponding resistance $R_{sm}$ change with the shape transformation of the shape memory member 100.

The driver circuit includes a power source, such as the voltage source shown, that drives the detection circuit 114, and a wheatstone bridge formed with the resistive element $R_{sm}$ of the strain gage of shape memory member 100 and a plurality of fixed resistors. The voltage detector 105 monitors the change in strain of the strain gage by monitoring the resistance of strain gage and generates the transformation data 104, for example, when the change in resistance $R_{sm}$ indicates that the shape transformation has occurred.

In an embodiment, the voltage detector 105 generates the transformation data 106 to indicate the shape transformation of the shape memory member from the catheterization shape to the transformed shape when the resistance $R_{sm}$ (corresponding to the strain of the strain gage) compares favorably to a transformation threshold. In particular, the transformation data 106 can include a data flag having a first value that indicates the catheterization shape and a second value that indicates the transformed shape. The transition of the transformation data from the first value to the second value can indicate that the transformation has occurred.

Figure 12:
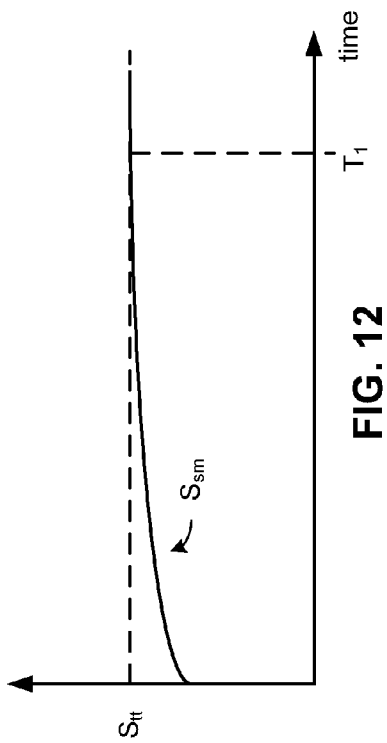
FIG. 12 is a graphical representation of a strain profile in accordance with an embodiment the present invention.

FIG. 12 is a graphical representation of a strain profile of in accordance with an embodiment the present invention. An example strain profile of a strain gage of shape memory member 100 is shown. As the shape memory member is heated in conjunction with the deployment of the shape memory catheterization device, the strain, $S_{sm}$, changes with time. In particular, the strain $S_{sm}$ changes in response to the shape transformation of the shape memory member caused by the heating of the shape memory catheterization device.

As discussed in conjunction with FIG. 11, the voltage detector 105 generates the transformation data 106 to indicate the shape transformation of the shape memory member from the catheterization shape to the transformed shape when the resistance $R_{sm}$ corresponding to the strain $S_{sm}$ of the strain gage compares favorably to a transformation threshold. In the example shown, the transformation over time of the shape memory member causes the strain $S_{sm}$ to increase. At a time, $T_1$, the strain $S_{sm}$ reaches a transition threshold, $S_{tt}$, and stabilizes indicating the shape transformation is complete. In this example the voltage detector can include a comparator that generates the transformation data 106 when the $S_{sm}$ meets or exceeds the transition threshold, $S_{tt}$.

While the transformation over time of the shape memory member causes the strain $S_{sm}$ to increase in the example shown, in other examples, the strain may decrease depending on the nature of the original and catheterization shape of the shape memory member and/or the nature, position and orientation of the strain gage or gages included in the shape memory member, etc. Further, while the voltage detector has been described in terms of comparing the strain $S_{sm}$ to a transition threshold, $S_{tt}$, other metrics such as the stabilization of the strain $S_{sm}$ can likewise be employed.

Further, while the embodiments above contemplate a shape memory device with a single strain gage, multiple strain gages can be driven and monitored by transformation data generator 102. For example, strain gages can be placed at multiple points, on multiple axes of transformation or otherwise on multiple portions of a shape memory member 100. In this configuration, transformation data 106 can be generated to indicate the transform shape when all of the strain gages indicate a transformation has taken place.

FIG. 13 is a pictorial representation of the shape transformation of a shape memory member of in accordance with an embodiment the present invention. In particular, a shape memory member 100 is presented as a cylinder. Examples of such shape memory members include a cylindrical tube constructed with shape memory polymer for grafting a vein or artery to treat an aneurism or a cylindrical tube constructed with shape memory polymer or cylindrical mesh constructed with either a shape memory polymer or shape memory alloy for supporting a vein or artery after removing a blockage. In the configuration shown, the shape memory member 100 is fitted on a delivery rod to be delivered through a delivery rod 150 (a portion of which is shown schematically) and is deformed from an original shape 120 into a catheterization shape 122 with reduced diameter via crimping. When the shape memory member 100 is heated during deployment, it transforms into the transformed shape 124 that is substantially the original shape 120, subject to, for example, physical conformity to the tissue, such as the vein, artery or other tissue in which the shape memory catheterization device is deployed.

While the catheterization shape 122 is shown as cylindrical, other shapes are possible including a flattened cylinder, and other shapes, based on the particular method of deformation and further based on the desired shape for catheterization. Further, while the original shape 120 is shown as cylindrical, other regular geometrical shapes such as spherical, pyramidal, etc. could likewise be employed as well as any number of irregular shapes, based on the desired shape for deployment of the shape memory member 100.

It should be noted that the shape memory member 100 can be detached from the delivery rod 150 after being placed in the proper tissue location for deployment and left in the patient. In embodiments where the shape memory member 100 includes a shape memory polymer, the shape memory polymer can be doped with a drug, such as an anticoagulant to reducing clotting, a drug to promote acceptance of the device by the surrounding tissue or other drug.

FIG. 14 is a pictorial representation of the transformation of a shape memory member of in accordance with an embodiment the present invention. In particular, a shape memory member 100 is presented as a cylinder. Examples of such shape memory members include a cylindrical cup for holding a drug for intravenous deployment. In the configuration shown, the closed end of the cup is fitted to a delivery rod 150, (the end of which is shown schematically) and the inner portion of the cup is packed with the drug to be deployed via the open end 121 and is then deformed from an original shape 120 into a catheterization shape 123 via crimping. As shown the open end 121 of the original shape 120 is closed in the catheterization shape 123 to hold the drug for catheterization in a pocket 125 for deployment. When the shape memory member 100 is heated during deployment, it transforms into transformed shape 124 that is substantially the original shape 120, subject to, for example, physical conformity to the tissue, such as the vein, artery or other tissue in which the shape memory device is deployed. The end 121 of the cup opens for release of the drug.

While the catheterization shape 122 is shown as cylindrical, other shapes are possible including a flattened cylinder, and other shapes, based on the particular method of deformation and further based on the desired shape for catheterization. Further, while the original shape 120 is shown as cylindrical, other regular geometrical shapes such as spherical, pyramidal, etc. could likewise be employed as well as any number of irregular shapes, based on the desired shape for deployment of the shape memory member.

It should be noted that the shape memory member 100 can remain attached to the delivery rod 150 after being placed in the proper tissue location for deployment and removed from the patient after the drug is released. In embodiments where the shape memory member includes a shape memory polymer, the shape memory polymer can also be doped with a drug, such as an anticoagulant to reducing clotting, or other drug.

FIG. 15 is a pictorial representation of the transformation of a shape memory member of in accordance with an embodiment the present invention. In particular, a shape memory member 100 is presented as a cylinder. Examples of such shape memory members include a cylindrical with a spherical pocket 126 for holding a drug for intravenous deployment. In the configuration shown, the cylinder is fitted to a delivery rod 150, (the end of which is shown schematically) and the pocket 126 is packed with the drug to be deployed and is then deformed from an original shape 125 into a catheterization shape 127 via crimping a portion of the cylinder shown. As shown, the pocket 126 of the original shape 125 is closed in the catheterization shape 127 to hold the drug for catheterization in a pocket 126 for deployment. When the shape memory member 100 is heated during deployment, it transforms into transformed shape 129 that is substantially the original shape 125, subject to, for example, physical conformity to the tissue, such as the vein, artery or other tissue in which the shape memory device is deployed. The pocket 126 opens for release of the drug.

While the catheterization shape 127 is shown as cylindrical, other shapes are possible including a flattened cylinder, and other shapes, based on the particular method of deformation and further based on the desired shape for catheterization. Further, while the original shape 125 is shown as cylindrical, other regular geometrical shapes such as a spherical, pyramidal, etc. could likewise be employed as well as any number of irregular shapes, based on the desired shape for deployment of the shape memory member. In a further embodiment, the shape memory member can be a hollow cup that is crimped to hold the ball end of a medical device and that releases the ball end for deployment. Further, while a single pocket 126 is shown, a shape memory member 100 with multiple pockets could be implemented in a similar fashion.

It should be noted that the shape memory member 100 can remain attached to the delivery rod 150 after being placed in the proper tissue location for deployment and removed from the patient after the drug is released. Delivery rod 150 includes a plurality of electrodes 130 and 132 that electrically couple to the shape memory member 100. In operation, the electrodes couple a transformation data generator 110 to a capacitive, resistive element or an inductive element of shape memory member 100 or a strain gage coupled thereto. The plurality of electrodes are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

In embodiments where the shape memory member 100 includes a shape memory polymer, the shape memory polymer can also be doped with a drug, such as an anticoagulant to reducing clotting, or other drug. While a particular medical device is shown, other medical devices can similarly be deployed. Further, while the medical device is shown with a ball end, other catch designs including a pyramidal catch, a box catch or other shapes can likewise be implemented FIG. 16 is a pictorial representation of the transformation of a shape memory member of in accordance with an embodiment the present invention. In particular, a shape memory member 100 is shown along with electrodes 130 and 132 that electrically couple to the shape memory member. The electrodes can be part of a delivery rod such as delivery rod 150, not specifically shown.

In various embodiments, the shape memory member 100 can be detached from the delivery rod 150 after being placed in the proper tissue location for deployment and left in the patient. In these embodiments, the plurality of electrodes 130 and 132 decouple from the shape memory member 100 when the shape memory member 100 is detached from the delivery rod 150. In embodiments where the shape memory member 100 remains attached to the delivery rod and is removed from the patient's body after treatment the electrodes 130 and 132 can be more permanently attached to the shape memory member 100.

In operation, the electrodes couple a transformation data generator 110 to a resistive element or an inductive element of shape memory member 100. As previously discussed, the shape memory member can be a shape memory polymer with electrically resistive or inductive properties, that is surface doped with a conductive or partially conductive compound, or that is doped to saturation with a conductive or partially conductive compound. In a further example the shape memory member can be formed of a shape memory polymer to include a flexible resistive or inductive member such as a metallic foil element adhered or deposited on the surface of the shape memory member, a flexible foil or coil insert, a resistive foam member or insert or other resistive or inductive member. In addition, the shape memory member can be formed of a shape memory alloy that is electrically conductive with either a resistance or inductance that changes in response to the shape transformation of the shape memory member 100.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

FIG. 17 is a pictorial representation of the transformation of a shape memory member of in accordance with an embodiment the present invention. As in the embodiment of FIG. 16, a shape memory member 100 is shown along with electrodes 130 and 132 that electrically couple to the shape memory member. In this embodiment, the electrodes couple a transformation data generator 110 to a capacitive element of shape memory member 100 via conductive plates 134 and 136. The plates 134 and 136 can be constructed of metallic foil elements adhered or deposited on the surface of the shape memory member, conductive foam members or inserts or other conductive member. The shape memory element 100 can be doped with an electrolytic compound to increase the capacitance of the device.

FIG. 18 is a pictorial representation of the transformation of a shape memory member of in accordance with an embodiment the present invention. As in the embodiment of FIGS. 16 and 17, a shape memory member 100 is shown along with electrodes 130 and 132 that electrically couple to the shape memory member. In this embodiment, the electrodes couple a transformation data generator 110 to a strain gage 136 of shape memory member 100. The strain gage can be constructed of metallic foil elements adhered or deposited on the surface of the shape memory member, conductive foam members or inserts or other strain gage configurations.

FIG. 19 is a pictorial representation of the transformation of a shape memory member of in accordance with an embodiment the present invention. In particular, a shape memory member 100 is presented as a coil. Examples of such shape memory members include a coil constructed with shape memory alloy or shape memory polymer to treat an aneurism by filling a weakened portion of a vein or artery. In the configuration shown, the shape memory member 100 is fitted on a catheter (not shown) and is deformed from an original shape 140 into a catheterization shape 142. When the shape memory member 100 is heated during deployment, it transforms into transformed shape 144 that is substantially the original shape 140, subject to, for example, physical conformity to the tissue, such as the vein, artery or other tissue in which the shape memory catheterization device is deployed.

The shape memory member 100 can be constructed of a resistive or conductive wire or other resistive or conductive material that is biocompatible. The shape transformation of the shape memory member 100 can be detected based on a change of resistance or inductance of the shape memory member.

It should be noted that the shape memory member 100 can be detached from the delivery rod 150 after being placed in the proper tissue location for deployment and left in the patient. In embodiments where the shape memory member includes a shape memory polymer, the shape memory polymer can be doped with a drug, such as an anticoagulant to reducing clotting, a drug to promote acceptance of the device by the surrounding tissue or other drug.

FIG. 20 is a pictorial representation of the transformation of a shape memory member of in accordance with an embodiment the present invention. In particular, a shape memory member 100 is presented as a cylinder. Examples of such shape memory members include a cylinder with a spherical pocket 126 for holding a medical device 146 such as a coil for intravenous deployment for treatment of an aneurism.

In the configuration shown, the shape memory member 100 is fitted to a delivery rod 150, (the end of which is shown schematically) and the pocket 126 is packed with a catch, such as a ball end of the medical device 146 to be deployed. The shape memory device 100 is then deformed from an original shape 145 into a catheterization shape 147 via crimping a portion of the cylinder shown. As shown, the pocket 146 of the original shape 145 is closed in the catheterization shape 147 to hold the ball end medical device for catheterization in the pocket 126 for deployment. When the shape memory member 100 is heated during deployment, it transforms into transformed shape 149 that is substantially the original shape 125, subject to, for example, physical conformity to the tissue, such as the vein, artery or other tissue in which the shape memory device is deployed. The pocket 126 opens for release of the medical device 146. In the embodiment shown, the medical device 146 is itself constructed of a shape memory member, such as a shape memory wire, alloy or polymer that is compressed into a catheterization shape and that expands to its own transformed shape for treatment.

While the catheterization shape 147 is shown as cylindrical, other shapes are possible including a flattened cylinder, and other shapes, based on the particular method of deformation and further based on the desired shape for catheterization. Further, while the original shape 145 is shown as cylindrical, other regular geometrical shapes such as spherical, pyramidal, etc. could likewise be employed as well as any number of irregular shapes, based on the desired shape for deployment of the shape memory member. Further, while a single pocket 146 is shown, a shape memory member 100 with multiple pockets could be implemented in a similar fashion.

It should be noted that the shape memory member 100 can remain attached to the delivery rod 150 after being placed in the proper tissue location for deployment and removed from the patient after the medical device 146 is released. Delivery rod 150 includes a plurality of electrodes 130 and 132 that electrically couple to the shape memory member 100. In operation, the electrodes couple a transformation data generator 110 to a capacitive, resistive element or an inductive element of shape memory member 100 or a strain gage coupled thereto. The plurality of electrodes are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

In embodiments where the shape memory member 100 includes a shape memory polymer, the shape memory polymer can also be doped with a drug, such as an anticoagulant to reducing clotting, or other drug.

Figure 22:
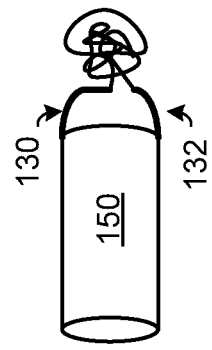
FIG. 22 is a pictorial representation of a shape memory member and catheter in accordance with an embodiment the present invention.
Figure 21:
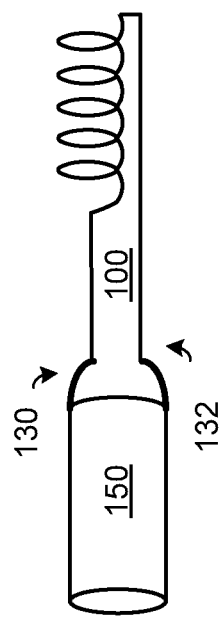
FIG. 21 is a pictorial representation of a shape memory member and catheter in accordance with an embodiment the present invention.

FIGS. 21 and 22 present pictorial representations of a shape memory member and delivery rod in accordance with an embodiment the present invention. Like the embodiment of FIG. 19, a shape memory member 100 is presented as a coil such as a coil constructed with shape memory alloy or shape memory polymer for to treat an aneurism by filling a weakened portion of a vein or artery. In the configuration shown, the shape memory member 100 is fitted on a delivery rod 150 and is deformed from an original shape shown in FIG. 21 into a catheterization shape shown in FIG. 22. When the shape memory member 100 is heated during deployment, it transforms into transformed shape that is substantially the original shape, subject to, for example, physical conformity to the tissue, such as the vein, artery or other tissue in which the shape memory catheterization device is deployed.

It should be noted that the shape memory member 100 can be detached from the delivery rod 150 after being placed in the proper tissue location for deployment and left in the patient. Delivery rod 150 includes a plurality of electrodes 130 and 132 that electrically couple to the shape memory member 100 and that decouple from the shape memory member 100 when the shape memory member 100 is detached from the delivery rod 150. In operation, the electrodes couple a transformation data generator 110 to a capacitive, resistive element or an inductive element of shape memory member 100 or a strain gage coupled thereto. The plurality of electrodes 130 and 132 are electrically coupled to a portion of the shape memory member 100 to detect a change in resistance, capacitance or inductance of the shape memory member caused by the shape transformation of the shape memory member 100 during deployment.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example, the plurality of electrodes 130 and 132 can be formed a flexible conductive foam member or insert or other conductive member. It should be noted that the shape memory member 100 can be detached from the delivery rod 150 and electrodes 130 and 132 after being placed in the proper tissue location for deployment and left in the patient.

Figure 23:
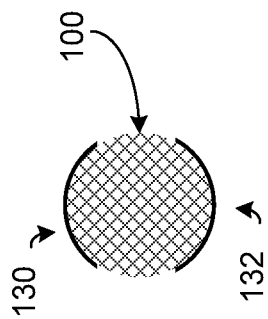
FIG. 23 is a pictorial representation of a shape memory member and catheter in accordance with an embodiment the present invention.

FIG. 23 is a pictorial representation of a shape memory member and catheter in accordance with an embodiment the present invention. In particular, a cross section is shown of a cylindrical shape memory member 100 and electrodes 130 and 132. In this embodiment the electrodes are arc shaped to conform with the outer surface of the cylindrical shape memory member 100. While each electrode 130 or 132 is shown as a single homogeneous element, each electrode can include a central palm and a plurality of fingers each having a longitudinal axis along the longitudinal axis of the cylindrical shape memory member 100. In this configuration, the fingers of each electrode lend themselves to being crimped into a position of contact when the shape memory member 100 is deformed for catheterization and to remain in contact with the shape memory member 100 when the shape memory member 100 undergoes its shape transformation.

Figure 24:
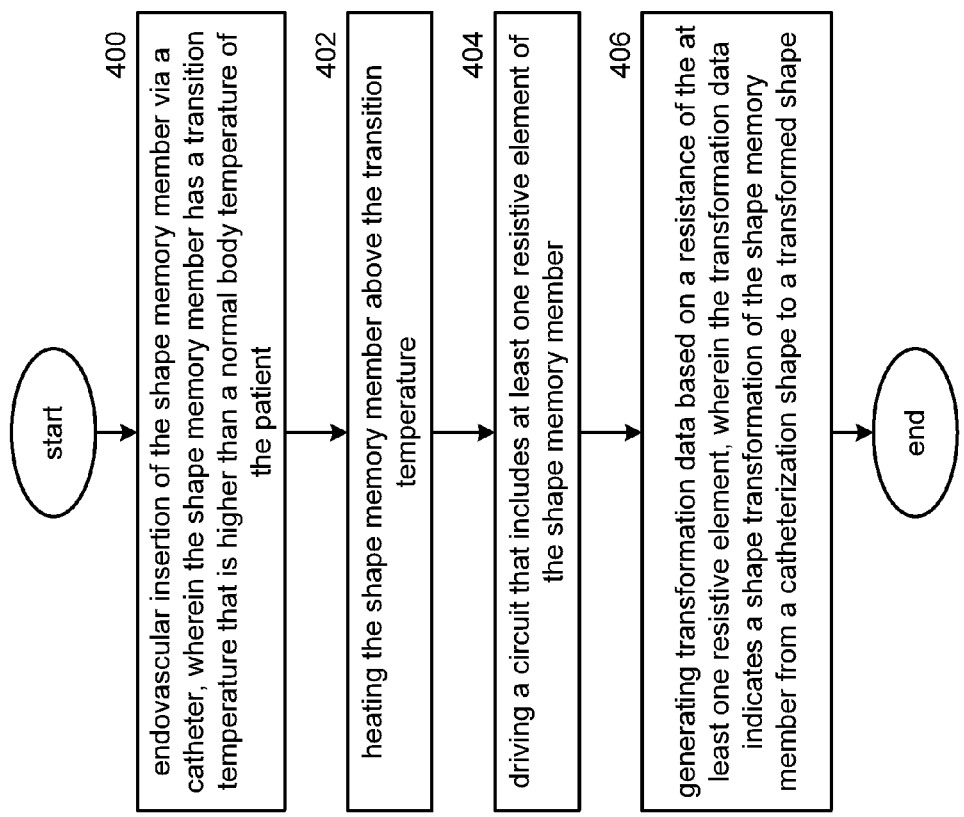
FIG. 24 is a flowchart representation of an embodiment of a method in accordance with the present invention.

FIG. 24 is a flowchart representation of an embodiment of a method in accordance with the present invention. In particular, a method is presented for use in conjunction with one or more features and functions described in conjunction with FIGS. 1-23. Step 400 includes endovascular insertion of the shape memory member via a catheter, wherein the shape memory member has a transition temperature that is higher than a normal body temperature of the patient. Step 402 includes heating the shape memory member above the transition temperature. Step 404 includes driving a circuit that includes at least one resistive element of the shape memory member. Step 406 includes generating transformation data based on a resistance of the at least one resistive element, wherein the transformation data indicates a shape transformation of the shape memory catheterization device from a catheterization shape to a transformed shape.

In an embodiment, the transformation data is generated to indicate the shape transformation of the shape memory member from the catheterization shape to the transformed shape when the resistance of the at least one resistive element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 25:
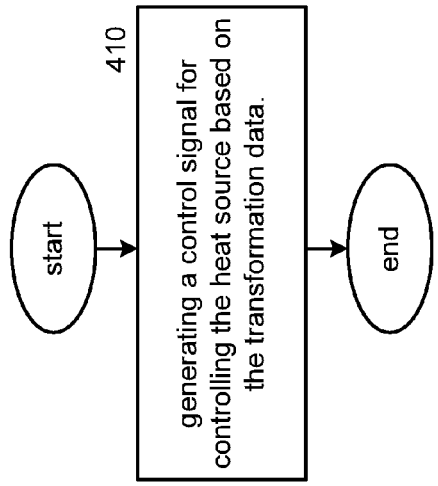
FIG. 25 is a flowchart representation of an embodiment of a method in accordance with the present invention.

FIG. 25 is a flowchart representation of an embodiment of a method in accordance with the present invention. In particular, a method is presented for use in conjunction with one or more features and functions described in conjunction with FIGS. 1-24. Step 410 includes generating a control signal for controlling the heat source based on the transformation data. In an embodiment, a control signal is generated to discontinue the heating of the shape memory member when the transformation data indicates the shape transformation of the shape memory member from the catheterization shape to the transformed shape.

Figure 26:
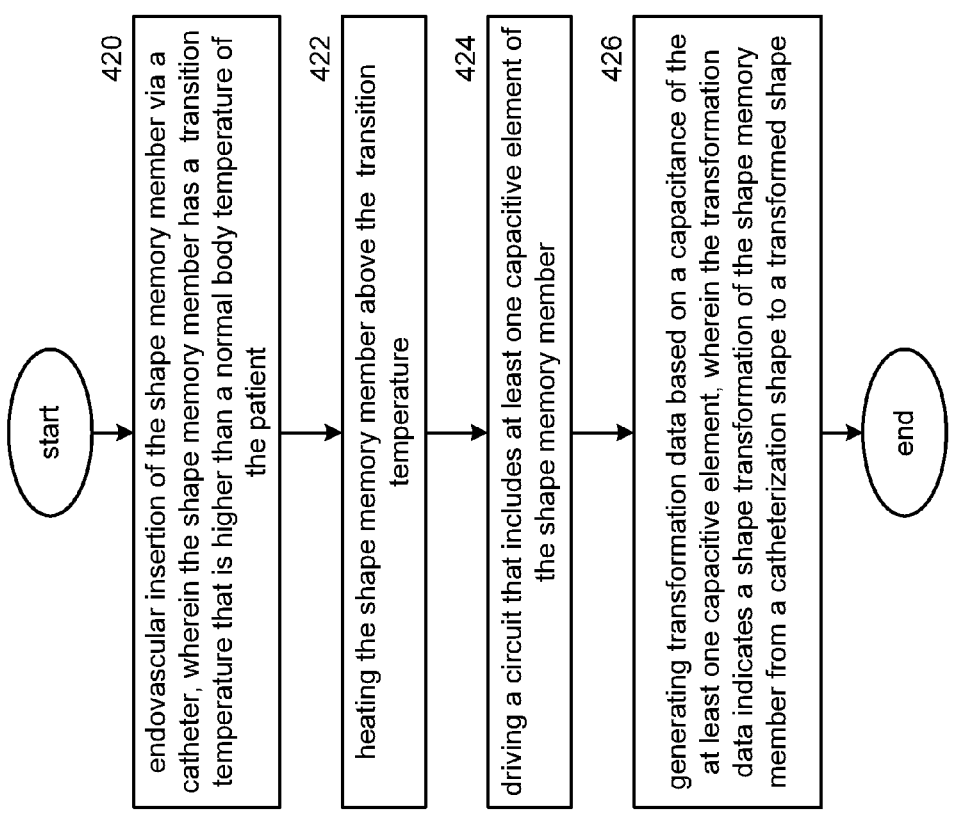
FIG. 26 is a flowchart representation of an embodiment of a method in accordance with the present invention.

FIG. 26 is a flowchart representation of an embodiment of a method in accordance with the present invention. In particular, a method is presented for use in conjunction with one or more features and functions described in conjunction with FIGS. 1-25. Step 420 includes endovascular insertion of the shape memory member via a delivery rod through a catheter, wherein the shape memory member has a transition temperature that is higher than a normal body temperature of the patient. Step 422 includes heating the shape memory member above the transition temperature. Step 424 includes driving a circuit that includes at least one capacitive element of the shape memory member. Step 426 includes generating transformation data based on a capacitance of the at least one capacitive element, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the capacitance of the at least one capacitive element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 27:
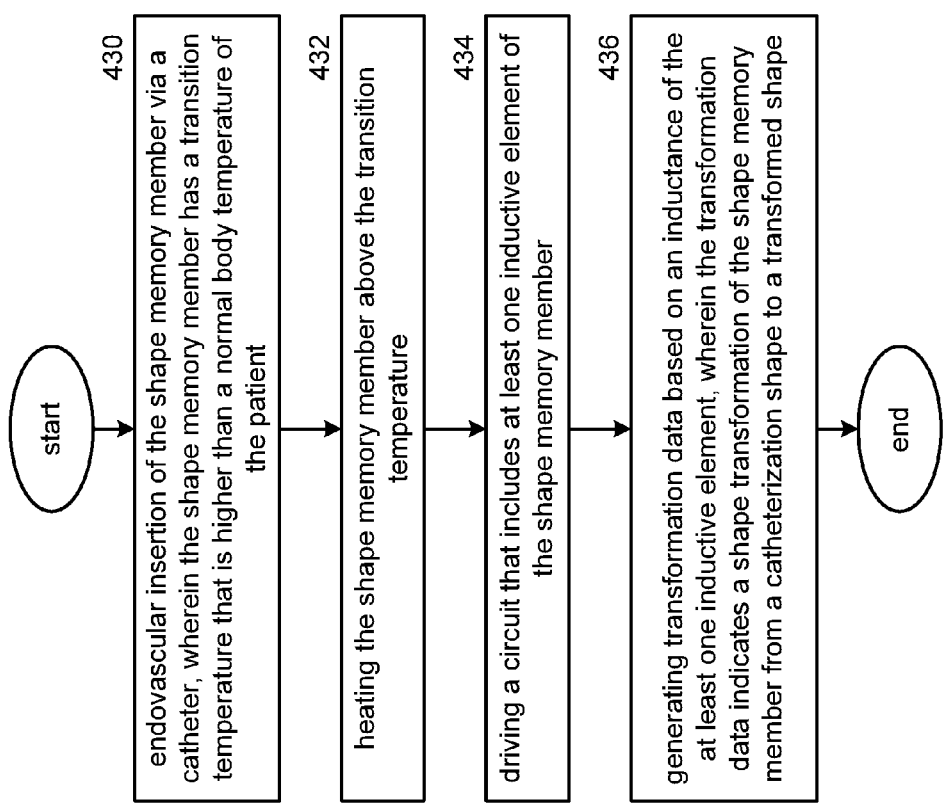
FIG. 27 is a flowchart representation of an embodiment of a method in accordance with the present invention.

FIG. 27 is a flowchart representation of an embodiment of a method in accordance with the present invention. In particular, a method is presented for use in conjunction with one or more features and functions described in conjunction with FIGS. 1-26. Step 430 includes endovascular insertion of a shape memory member via a delivery rod through a catheter, wherein the shape memory member has a transition temperature that is higher than a normal body temperature of the patient. Step 432 includes heating the shape memory member above the transition temperature. Step 434 includes driving a circuit that includes at least one inductive element of the shape memory member. Step 436 includes generating transformation data based on an inductance of the at least one inductive element, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the inductance of the at least one inductive element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 28:
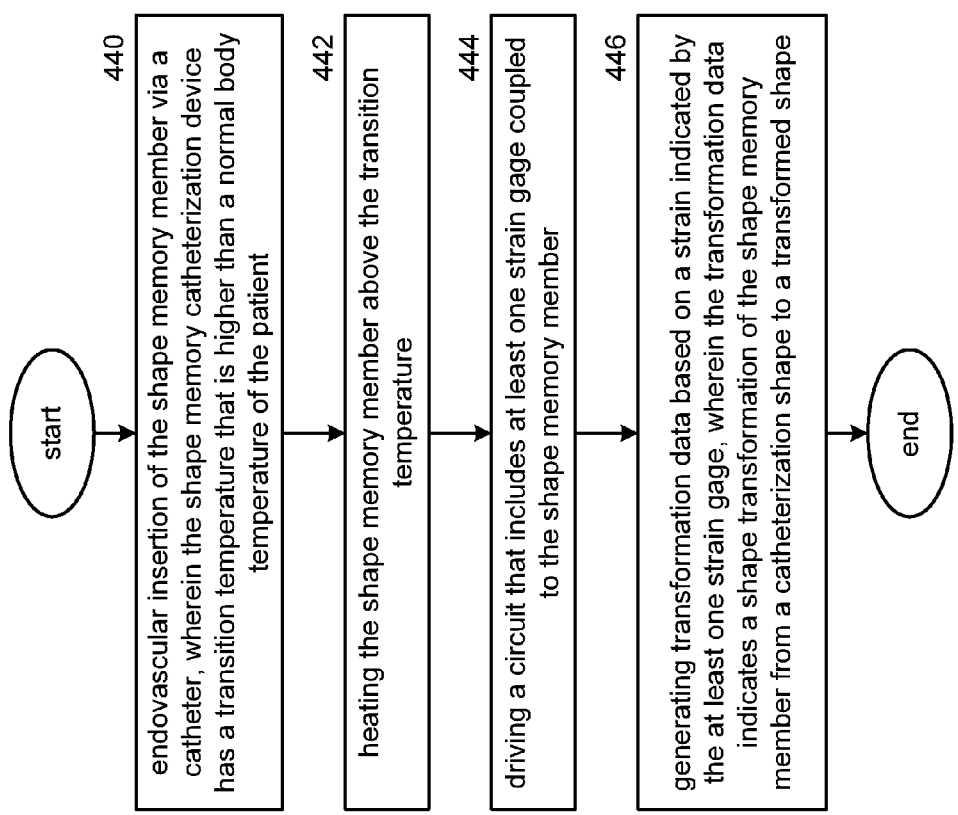
FIG. 28 is a flowchart representation of an embodiment of a method in accordance with the present invention.

FIG. 28 is a flowchart representation of an embodiment of a method in accordance with the present invention. In particular, a method is presented for use in conjunction with one or more features and functions described in conjunction with FIGS. 1-27. Step 440 includes endovascular insertion of the shape memory member via a delivery rod through a catheter, wherein the shape memory member has a transition temperature that is higher than a normal body temperature of the patient. Step 442 includes heating the shape memory member above the transition temperature. Step 444 includes driving a circuit that includes at least one strain gage coupled to the shape memory member. Step 446 includes generating transformation data based on a strain indicated by the at least one strain gage, wherein the transformation data indicates a shape transformation of the shape memory member from a catheterization shape to a transformed shape.

In an embodiment, the transformation data is generated to indicate the shape transformation of the shape memory member from the catheterization shape to the transformed shape when the strain indicated by the at least one strain gage element compares favorably to a transformation threshold. The transformation data can includes a data flag having a first value that indicates the catheterization shape and a second value that indicates the transformed shape.

The shape memory catheterization device can include an endovascular stent for treating a blocked artery, an endovascular stent for treating an arterial aneurism. The shape memory catheterization device can intravenously deploy a drug or a medical device in response to the shape transformation of the shape memory member from the catheterization shape to the transformed shape. The shape memory member can be doped to intravenously deploy a drug.

Figure 29:
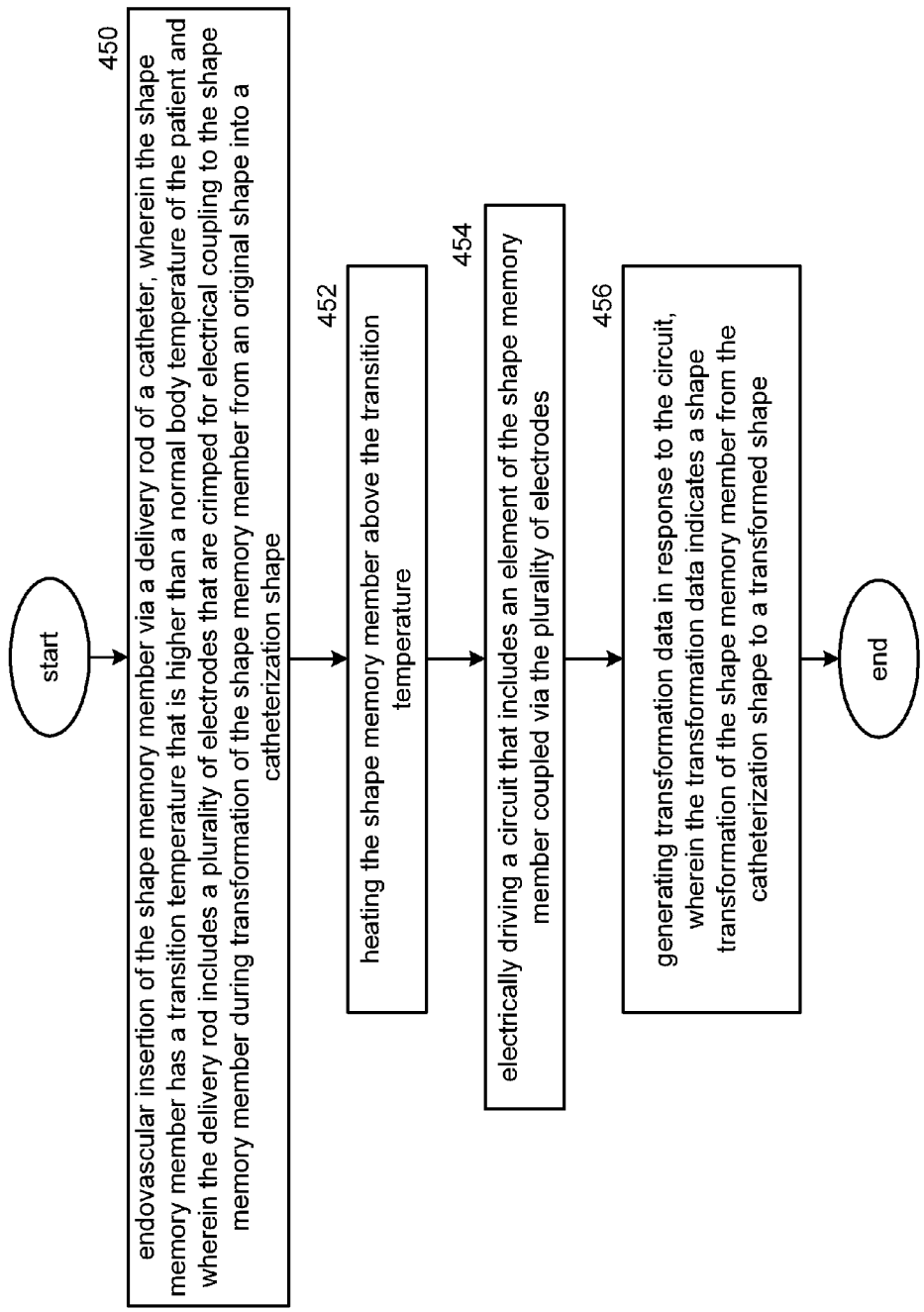
FIG. 29 is a flowchart representation of an embodiment of a method in accordance with the present invention.

FIG. 29 is a flowchart representation of an embodiment of a method in accordance with the present invention. In particular, a method is presented for use in conjunction with one or more features and functions described in conjunction with FIGS. 1-28. Step 450 includes endovascular insertion of a shape memory member via a delivery rod through a catheter, wherein the shape memory member has a transition temperature that is higher than a normal body temperature of the patient and wherein the catheter includes a plurality of electrodes that are crimped for electrical coupling to the shape memory member during transformation of the shape memory member from an original shape into a catheterization shape. Step 452 includes heating the shape memory member above the transition temperature. Step 454 includes electrically driving a circuit that includes an element of the shape memory member coupled via the plurality of electrodes. Step 456 includes generating transformation data in response to the circuit, wherein the transformation data indicates a shape transformation of the shape memory member from the catheterization shape to a transformed shape.

In an embodiment, the circuit is electrically driven by either a direct current or an alternative current. The shape memory catheterization device can include an endovascular stent for treating a blocked artery or an endovascular stent for treating an arterial aneurism. The shape memory catheterization device can intravenously deploy a drug in response to the shape transformation of the shape memory member from the catheterization shape to the transformed shape. The shape memory catheterization device can intravenously deploy a drug. The shape memory catheterization device can intravenously deploy a medical device in response to the shape transformation of the shape memory member from the catheterization shape to the transformed shape. The transformation data can include a data flag having a first value that indicates the catheterization shape and a second value that indicates the transformed shape.

Figure 30:
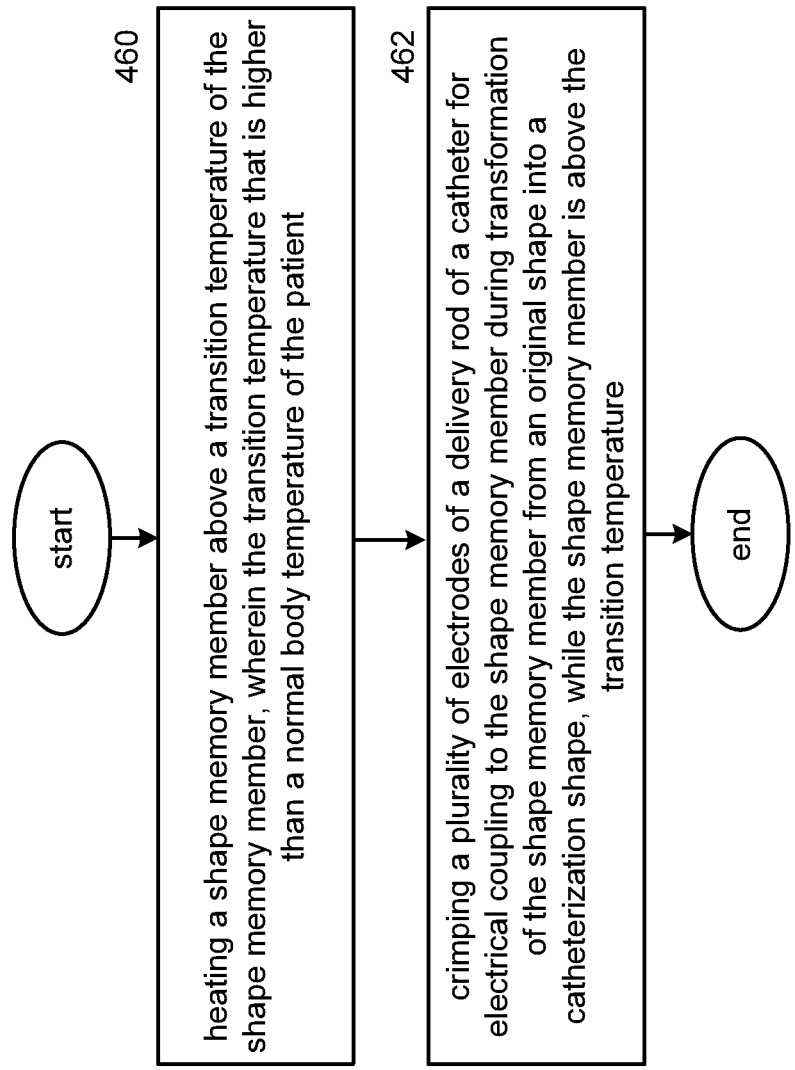
FIG. 30 is a flowchart representation of an embodiment of a method in accordance with the present invention.

FIG. 30 is a flowchart representation of an embodiment of a method in accordance with the present invention. In particular, a method is presented for use in conjunction with one or more features and functions described in conjunction with FIGS. 1-29. Step 460 includes heating a shape memory member above a transition temperature of the shape memory member, wherein the transition temperature that is higher than a normal body temperature of the patient. Step 462 includes crimping a plurality of electrodes of a catheter for electrical coupling to the shape memory member during transformation of the shape memory catheterization device from an original shape into a catheterization shape, while the shape memory catheterization device is above the transition temperature.

The shape memory catheterization device can include an endovascular stent for treating a blocked artery or an endovascular stent for treating an arterial aneurism. The shape memory catheterization device can intravenously deploy a drug in response to the shape transformation of the shape memory member from the catheterization shape to the transformed shape. The shape memory catheterization device can intravenously deploy a drug. The shape memory catheterization device can intravenously deploy a medical device in response to the shape transformation of the shape memory member from the catheterization shape to the transformed shape.

Figure 31:
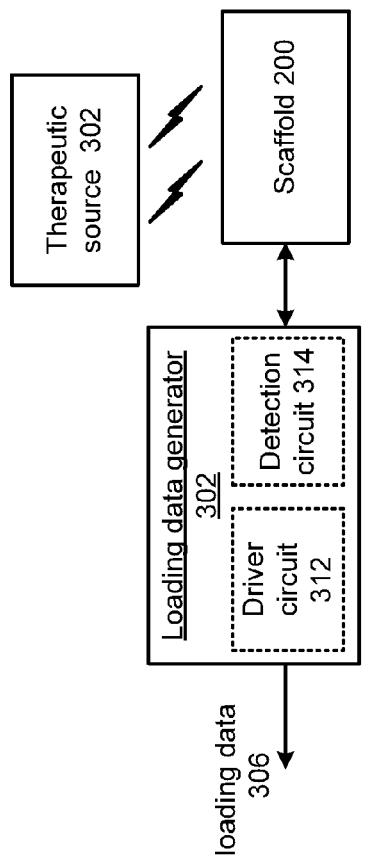
FIG. 31 is a schematic block diagram of an embodiment of a system for monitoring a scaffold 200 in accordance with the present invention.

FIG. 31 is a schematic block diagram of an embodiment of a system for monitoring a scaffold 200 in accordance with the present invention. In particular, scaffold 200 may be a shape-memory polymer or other scaffold material adhered or otherwise attached to a pushing rod or other delivery rod for targeted delivery, preferably through a catheter. This scaffold may be impregnated by loaded with drugs, cells, or genetic material (as in the case of gene therapy), or other therapeutic materials from therapeutic source 302.

A loading data generator 302 includes a driving circuit 312 that is electrically coupled to drive an impedance of the scaffold 200. A detection circuit 314 generates loading data 306 based on the impedance of the scaffold 200, such as a capacitance, resistance, inductance or some combination thereof. The loading data 306 uses the impedance measurement to indicate an amount of impregnation of the therapeutic material in the scaffold 200, such as via a loading profile, an unloading profile or other function of the impedance of the scaffold 200.

In one mode of operation, the therapeutic source 302 presents the therapeutic material to the scaffold 200 for loading. The therapeutic material may be present as a solid, liquid, solution, a colloid, such as a gel, emulsion, slurry or other form. The loading of the scaffold 200 can be performed via absorption, deposition, doping, osmosis, implantation or other loading of the scaffold with the therapeutic material from the therapeutic source 302. In one example of operation, the scaffold 200 may be doped with biocompatible nano-particles. The nano-particles, such as gold nano-particles, are visible via external imaging modalities, such as medical ultrasound. The nano-particles may be spatially oriented in such a way as to provide a visual indication of the degree of degradation of the scaffold and therefore the degree of therapeutic substance delivery. They also provide a way for a user to confirm degradation is occurring or has completed. These nano-particles can be sized to elute from the body as waste. In this way, the scaffold may be monitored non-invasively, in vivo.

The loading data generator 302 is electrically coupled to the scaffold 200 to monitor the loading of the therapeutic material based on a change in impedance of the scaffold. In particular, the impedance of the scaffold 200 can be measured at a number of time points to allow for analysis. These may include the time at which the scaffold 200 is unloaded and undelivered, the scaffold is loaded and undelivered, and various time points during which the scaffold is delivered and in the process of unloading. Here loading refers to the concentration of therapeutic substance within the scaffold and delivery refers to the scaffold's location, whether the device is being externally tested or applied internally or externally for therapeutic substance unloading.

The measurement of loading data 306 can be calibrated to provide a reading that represents the true concentration of the therapeutic material in the scaffold 200. In an embodiment, multiple impedances of the scaffold can be measured via three or more electrodes to provide several spatially diverse impedance measurements. The loading data 306 can be spatially calibrated and spatially measured to provide, for example, an image of the scaffold indicating resistance, capacitance, inductance or concentration measurements throughout the volume of the scaffold. These measurements may be used as a baseline for the scaffolds inherent resistance, capacitance, inductance or concentration. Further, the baseline measurement may be used to provide a more accurate loading reading.

Once the scaffold 200 is determined to be substantially or adequately loaded, the scaffold can be prepared for delivery or stored for later use. In pertinent part, the loading data 306 can include a data flag or other indication that the impregnation/loading of the therapeutic material is complete. In the event of storage, the loading data 306 can be measured again prior to mounting on a delivery rod or other delivery device or after mounting but prior to catheterization to ensure that the scaffold 200 remains adequately loaded.

In a further mode of operation, the loading data generator 302 can optionally be electrically coupled to the scaffold 200 via the delivery rod or other delivery device in order to monitor the loading and/or unloading of the therapeutic material from the scaffold before or after delivery. For example, the loading of the scaffold could be performed after the scaffold is mounted on the delivery rod or other delivery device, and the loading data generator 302 can monitor the loading as described above and determine, for example, when the impregnation/loading is complete, adequately complete or substantially complete. As discussed above, the loading data 306 can be measured again prior to catheterization to ensure that the scaffold 200 remains adequately loaded or to provide a first baseline reading.

In examples where the scaffold 200 remains attached to the catheter delivery rod, the loading data 306 can be measured shortly after delivery in situ via catheterization to provide a further baseline reading for monitoring the unloading of the therapeutic material from the scaffold 200. The loading data 306 can be analyzed to track an unloading profile of the therapeutic material and further can provide an indication that the therapeutic material is adequately unloaded, i.e. that the desired amount of therapeutic material has been delivered by the scaffold to the patient in proximity to the site of the delivery. Once the loading data 306 indicates that unloading is complete the scaffold can be removed from the patient, such as by retracting the delivery rod through the catheter.

While the loading data generator 302 is described above in conjunction with the measurement of one or more impedances associated with the scaffold 200, in other embodiments, loading data generator 302 can measure other properties in addition to or in place of impedance. For example, loading data generator 302 can include a driver and detector coupled to the scaffold 200 that measure a spectral conductance, transmission or absorption of a light wave that is transmitted through the scaffold 200. In a further example, loading data generator 302 can include a driver and detector coupled to the scaffold 200 that measure a spectral conductance, transmission or absorption of a millimeter wave or other RF signal transmitted through the scaffold 200. In pertinent part, loading data generate 306 interacts with the scaffold 200 via measurements to monitor the loading and unloading of the therapeutic material from the scaffold 200. The detection circuit 314 can include a processor or other processing device or circuit.

Further embodiments that include several optional functions and features will be described in conjunction with FIGS. 32-47 that follow.

Figure 32:
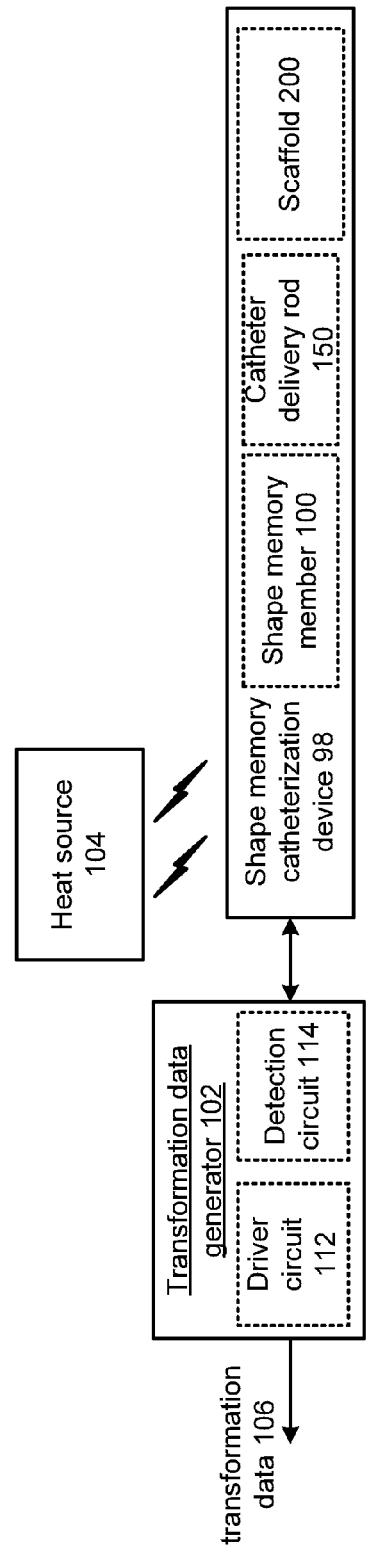
FIG. 32 is a schematic block diagram of an embodiment of a system for monitoring a scaffold 200 in accordance with the present invention.

FIG. 32 is a schematic block diagram of an embodiment of a system for monitoring a scaffold 200 in accordance with the present invention. In particular, a system is shown that is similar to the systems described in conjunction with FIGS. 1-30 where similar elements are referred to by common reference numerals. In this embodiment however, the scaffold 200 is either itself a shape memory member that operates in place of shape memory member 100 or is released by a shape memory member 100.

Consider first the example where the scaffold 200 is itself a shape memory member. In this example, the shape memory catheterization device 98 includes a catheter having a delivery rod 150 for use in conjunction with a catheterization procedure involving the insertion of the shape memory catheterization device 98 into a patient. Examples of such catheterization procedures include the insertion of an endovascular stent as part of an angioplasty or treatment of an aneurism or the intravenous deployment of another medical device, an intravenous drug deployment or the administration of anesthetic medication into the epidural space, the subarachnoid space, or around a major nerve bundle such as the brachial plexus, the administration of anesthetic medication into the epidural space, the subarachnoid space, or around a major nerve bundle such as the brachial plexus, an in vitro fertilization or other medical treatment, a urinary catheterization, treatment of an abdominal abscess, a balloon septostomy, balloon sinuplasty, catheter ablation, an in vitro fertilization or other medical treatment.

The shape memory catheterization device 98 includes a scaffold 200 that is implemented via a shape memory member having a transition temperature that is higher than a normal body temperature of the patient. When heat is applied by a heat source 104 the scaffold 200 of shape memory catheterization device 98 is heated above the transition temperature causes the scaffold to undergo a shape transformation from a catheterization shape into a transformed shape that is useful in the particular treatment. The heat source 104 can be an infrared emitter, laser or other light source, a heating coil or other electrical heating source, a microwave source or other electromagnetic source, a radiation source or other heat source. While shown separately from the shape memory catheterization device 98, the heat source 104 can be integrated into the shape memory catheterization device 98.

The transformation data generator 102 includes a driver circuit 112 and generates transformation data 106 based on feedback generated by the detection circuit 114. The transformation data 106 indicates a shape transformation of the scaffold 200 of the shape memory catheterization 98 device from the catheterization shape to the transformed shape. In an embodiment of the present invention the transformation data 106 can be displayed or otherwise used to provide visual, audible or tactile feedback to the users of shape memory catheterization device 98 that the shape memory member 100 has reached its transformation shape. The detection circuit 114 can include a processor or other processing device.

In second example, a shape memory member 100 provides a release mechanism for the scaffold 200. In an embodiment, the shape memory member 100 can remain attached to the delivery rod 150 after being placed in the proper tissue location for deployment and removed from the patient after the scaffold 200 is released. An example of such a shape memory member 100 includes a cylindrical cup for holding a scaffold 200 for intravenous deployment. In the configuration shown, the closed end of the cup is fitted to a delivery rod 150, (the end of which is shown schematically) and the inner portion of the cup is packed with the scaffold to be deployed via an open end and is then deformed from an original shape into a catheterization shape via crimping. When the shape memory member 100 is heated during deployment, it transforms into a transformed shape that is substantially the original shape, subject to, for example, physical conformity to the tissue, such as the vein, artery or other tissue in which the shape memory device is deployed. The cup opens for release of the scaffold.

Figure 33:
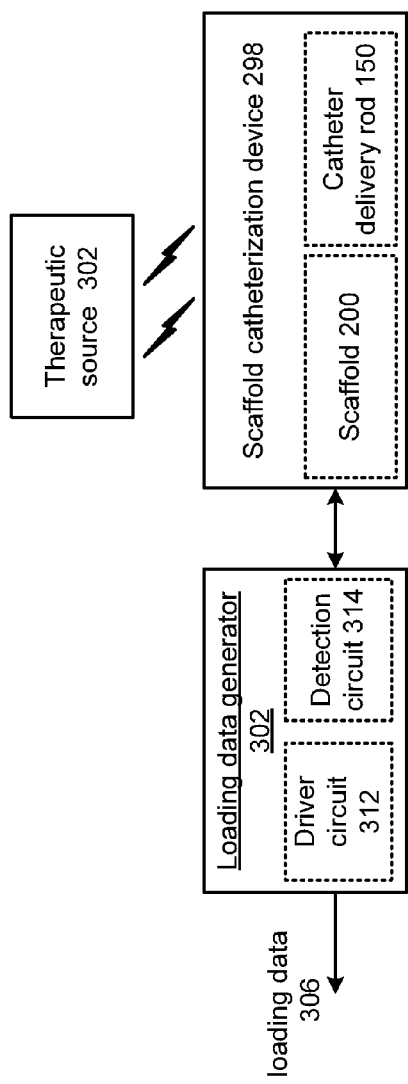
FIG. 33 is a schematic block diagram of an embodiment of a system for monitoring a scaffold 200 in accordance with the present invention.

FIG. 33 is a schematic block diagram of an embodiment of a system for monitoring a scaffold 200 in accordance with the present invention. As discussed in conjunction with FIG. 31, the scaffold 200 can be delivered via a scaffold catheterization device 298 that includes catheter delivery rod 150, such as a push rod or other delivery mechanism. In a further mode of operation, the loading data generator 302 can optionally be electrically coupled to the scaffold 200 via the delivery rod or other delivery device in order to monitor the loading and/or unloading of the therapeutic material from the scaffold before or after delivery.

In the example shown, the loading of the scaffold 200 via therapeutic source 302 is performed after the scaffold is mounted on the catheterization delivery rod 150. The loading data generator 302 monitors the loading as previously described and can determine, for example, when the impregnation/loading is complete. As discussed above, the loading data 306 can be measured again prior to catheterization to ensure that the scaffold 200 remains adequately loaded or to provide a first baseline reading.

In examples where the scaffold 200 remains attached to the catheter delivery rod 150, the loading data 306 can be measured shortly after delivery in situ via catheterization to provide a further baseline reading for monitoring the unloading of the therapeutic material from the scaffold 200. The loading data 306 can be analyzed to track an unloading profile of the therapeutic material and further can provide an indication that the therapeutic material is adequately unloaded, i.e. that the desired amount of therapeutic material has been delivered by the scaffold to the patient in proximity to the site of the delivery. Once the loading data 306 indicates that unloading is complete the scaffold 200 can be removed from the patient, such as by retracting the delivery rod through the catheter.

Figure 34:
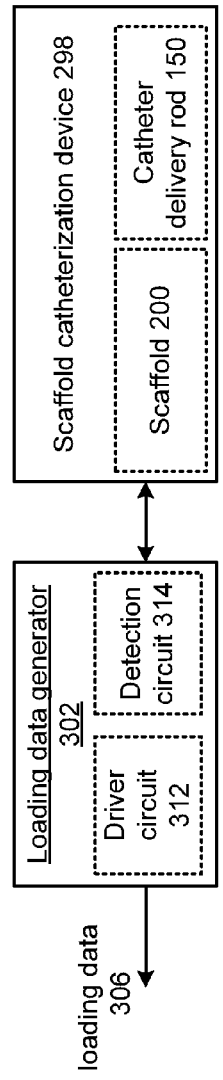
FIG. 34 is a schematic block diagram of an embodiment of a system for monitoring a scaffold 200 in accordance with the present invention.

FIG. 34 is a schematic block diagram of an embodiment of a system for monitoring a scaffold 200 in accordance with the present invention. As discussed in conjunction with FIGS. 31 and 33, the scaffold 200 can be delivered via a scaffold catheterization device 298 that includes catheter delivery rod 150, such as a push rod or other delivery mechanism. In a further mode of operation, the loading data generator 302 can optionally be electrically coupled to the scaffold 200 via the delivery rod or other delivery device in order to monitor the loading and/or unloading of the therapeutic material from the scaffold before or after delivery.

In the example shown, the loading of the scaffold 200 via therapeutic source 302 is performed prior to the scaffold being mounted on the catheterization delivery rod 150. The loading data generator 302 monitors the loading as previously described and the loading data 306 can be measured prior to mounting on the catheterization delivery rod 150 and/or after mounting but prior to catheterization to ensure that the scaffold 200 remains adequately loaded. Further, the loading data 306 can be measured shortly after delivery in situ via catheterization to provide a further baseline reading for monitoring the unloading of the therapeutic material from the scaffold 200.

The loading data 306 can be analyzed to track an unloading profile of the therapeutic material and further can provide an indication that the therapeutic material is adequately unloaded, i.e. that the desired amount of therapeutic material has been delivered by the scaffold to the patient in proximity to the site of the delivery. Once the loading data 306 indicates that unloading is complete, the scaffold 200 can be removed from the patient, such as by retracting the delivery rod through the catheter.

FIG. 35 is a graphical representation of a loading profile in accordance with an embodiment the present invention. In particular, a scaffold impedance, Z, is presented as a function of time during loading of therapeutic material in a scaffold, such as scaffold 200. As previously discussed, the impedance Z can represent a resistive impedance, a capacitive impedance, an inductive impedance or a combination thereof. While represented as a scalar quantity, the real portion, imaginary portion, the angle and/or the magnitude of the impedance can be used for similar purposes. As shown, the loading profile 252 indicates a change in impedance from the origin when loading begins, to a time $T_L$, where a loading threshold 250 is reached—indicating that that scaffold is adequately loaded.

It should be noted that while the loading profile is shown as a monotonically increasing function of increased concentration of the therapeutic material from an unloaded condition to a loaded condition, other functions, such as monotonically decreasing function or other functions can likewise be used, based on the composition of the scaffold 200, the nature of the therapeutic material in conjunction with the properties of any carrier used therewith such as a gel, solution, solid or other carrier.

In operation, the loading data generator 302 generates loading data 306 that indicate the loading profile 250, that provides specific data flags that indicates events such as certain benchmarks in loading completions (10%, 20%, 30% . . . ) and/or a further flag that indicates that the loading threshold 250 has been reached.

As described in conjunction with FIG. 31, loading data generator 302 can measure other properties in addition to or in place of impedance. For example, loading data generator 302 can include a driver and detector coupled to the scaffold 200 that measure a spectral conductance, transmission or absorption of a light wave that is transmitted through the scaffold 200. In a further example, loading data generator 302 can include a driver and detector coupled to the scaffold 200 that measure a spectral conductance, transmission or absorption of a millimeter wave or other RF signal transmitted through the scaffold 200. In pertinent part, loading data generate 306 interacts with the scaffold 200 via measurements to monitor the loading and unloading of the therapeutic material from the scaffold 200. In these further examples, loading data 306 can be generated based on loading profiles that present other quantities such as conductance, transmission or absorption of light or RF waves as a function of time as the concentration of the therapeutic material increases during loading.

FIG. 36 is a graphical representation of an unloading profile in accordance with an embodiment the present invention. In particular, a scaffold impedance, Z, is presented as a function of time during unloading of therapeutic material from a scaffold, such as scaffold 200. As previously discussed, the impedance Z can represent a resistive impedance, a capacitive impedance, an inductive impedance or a combination thereof. While represented as a scalar quantity, the real portion, imaginary portion, the angle and/or the magnitude of the impedance can be used for similar purposes. As shown, the unloading profile 262 indicates a change in impedance from the origin when loading begins to a time $T_U$, where an unloading threshold 260 is reached—indicating that that scaffold is adequately unloaded.

It should be notes that while the unloading profile is shown as a monotonically decreasing function of decreased concentration of the therapeutic material from an loaded condition to an unloaded condition, other functions, such as monotonically increasing function or other functions can likewise be used, based on the composition of the scaffold 200, the nature of the therapeutic material in conjunction with the properties of any carrier used therewith such as a gel, solution, solid of other carrier.

In operation, the loading data generator 302 generates loading data 306 that indicate the unloading profile 260, that provides specific data flags that indicates events such as certain benchmarks in unloading completions (10%, 20%, 30% . . . ) and/or a further flag that indicates that the unloading threshold 260 has been reached.

As described in conjunction with FIGS. 31 and 35, loading data generator 302 can measure other properties in addition to or in place of impedance. For example, loading data generator 302 can include a driver and detector coupled to the scaffold 200 that measure a spectral conductance, transmission or absorption of a light wave that is transmitted through the scaffold 200. In a further example, loading data generator 302 can include a driver and detector coupled to the scaffold 200 that measure a spectral conductance, transmission or absorption of a millimeter wave or other RF signal transmitted through the scaffold 200. In pertinent part, loading data generate 306 interacts with the scaffold 200 via measurements to monitor the loading and unloading of the therapeutic material from the scaffold 200. In these further examples, loading data 306 can be generated based on unloading profiles that present other quantities such as conductance, transmission or absorption of light or RF waves as a function of time as the concentration of the therapeutic material decreases during unloading.

FIG. 37 is a schematic block diagram of an embodiment of a loading data generator in accordance with the present invention. In this embodiment, the scaffold 200 includes a resistive element that has a resistance $R_s$ that changes in response to the concentration of the therapeutic material. For example, the scaffold can absorb, be doped, implanted with or otherwise carry a conductive or partially conductive therapeutic material or carrier thereof.

The driver circuit includes a power source, such as the voltage source shown, that drives the detection circuit 114 and a wheatstone bridge formed with the resistive element of the scaffold 200 and a plurality of fixed resistors. The voltage detector 105 monitors the change in resistance of the resistive element of the scaffold and generates the loading data 306, for example, that indicates the resistance or that indicates the change in resistance $R_s$ indicates that loading or unloading has occurred.

In an embodiment, the loading data 306 can include a data flag having a first value that indicates an unloaded condition and a second value that indicates a loaded condition. The transition of the loading 306 from the first value to the second value can indicate that loading has occurred. The transition of the loading 306 from the second value to the first value can indicate that unloading has occurred.

Figure 38:
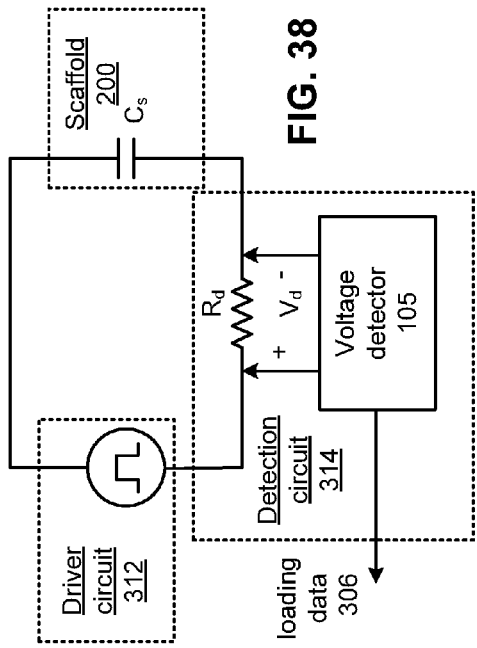
FIG. 38 is a schematic block diagram of an embodiment of a loading data generator in accordance with the present invention.

FIG. 38 is a schematic block diagram of an embodiment of a loading data generator in accordance with the present invention. In this embodiment, the scaffold 200 includes a capacitive element that has a capacitance $C_s$ that changes in response to the concentration of the therapeutic material. For example, the scaffold have capacitive properties, that is includes a plurality of plates that are surface doped with a conductive or partially conductive compound, a metallic foil element adhered or deposited on the surface of the shape memory member or a conductive foam or other conductive element that forms the plates. The scaffold further includes an electrolytic, dielectric or insulator that is disposed between the plurality of plates, wherein the electrolytic, dielectric or insulating properties changes the scaffold absorbs, be doped with, implanted with or otherwise carries therapeutic material or a carrier thereof.

The driver circuit 112 includes a power source, such as the voltage source shown, that drives the detection circuit 114 via an alternating current such as the step waveform generator that is shown. The driver circuit further includes a detection resistance $R_d$ that forms an RC circuit with the capacitive element of the scaffold 200. The voltage detector 105 monitors the change in capacitance of the capacitive element of scaffold 200 based on monitoring the time of charging and/or discharging of the capacitive element. The voltage detector generates the loading data 306, to indicate changes in capacitance $C_s$.

In an embodiment, the loading data 306 can include a data flag having a first value that indicates an unloaded condition and a second value that indicates a loaded condition. The transition of the loading 306 from the first value to the second value can indicate that loading has occurred. The transition of the loading 306 from the second value to the first value can indicate that unloading has occurred.

Figure 39:
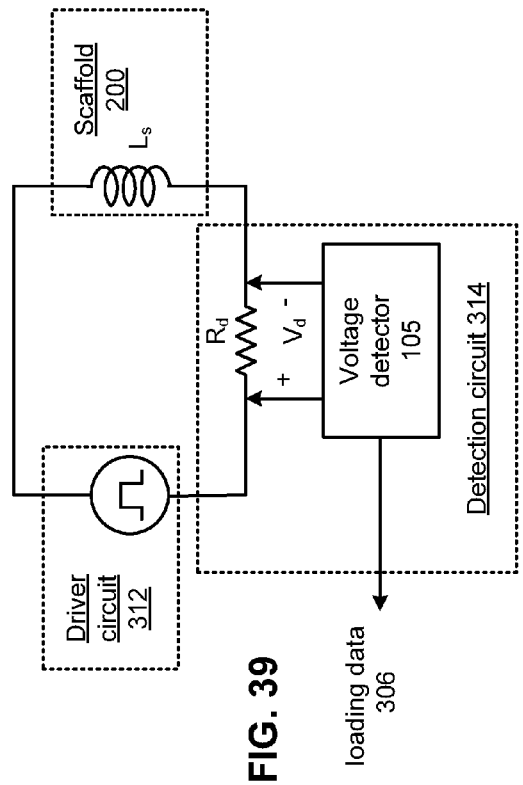
FIG. 39 is a schematic block diagram of an embodiment of a loading data generator in accordance with the present invention.

FIG. 39 is a schematic block diagram of an embodiment of a loading data generator in accordance with the present invention. In this embodiment, the scaffold 200 includes an inductive element that has an inductance $L_s$ that changes in response to the concentration of the therapeutic material. For example, the scaffold can have electrically inductive properties, that is surface doped with a conductive or partially conductive compound, or that is doped to saturation with a conductive or partially conductive compound. In a further example the scaffold 200 can include an inductive member such as a metallic foil element adhered or deposited on the surface of the scaffold, a flexible foil or coil insert, a conductive foam member or insert or other inductive member. For example, the scaffold can absorb, be doped, implanted with or otherwise carry a magnetically conductive or partially magnetically conductive therapeutic material or carrier thereof.

The driver circuit 112 includes a power source, such as the voltage source shown, that drives the detection circuit 114 via an alternating current such as the step waveform generator that is shown. The driver circuit further includes a detection resistance $R_d$ that forms an RL circuit with the inductive element of the scaffold 200. The voltage detector 105 monitors the change in inductance of the inductive element of scaffold 200 based on monitoring the time of charging and/or discharging of the inductive element. The voltage detector generates the loading data 306 to indicate changes in inductance $L_s$.

In an embodiment, the loading data 306 can include a data flag having a first value that indicates an unloaded condition and a second value that indicates a loaded condition. The transition of the loading 306 from the first value to the second value can indicate that loading has occurred. The transition of the loading 306 from the second value to the first value can indicate that unloading has occurred.

Figure 40:
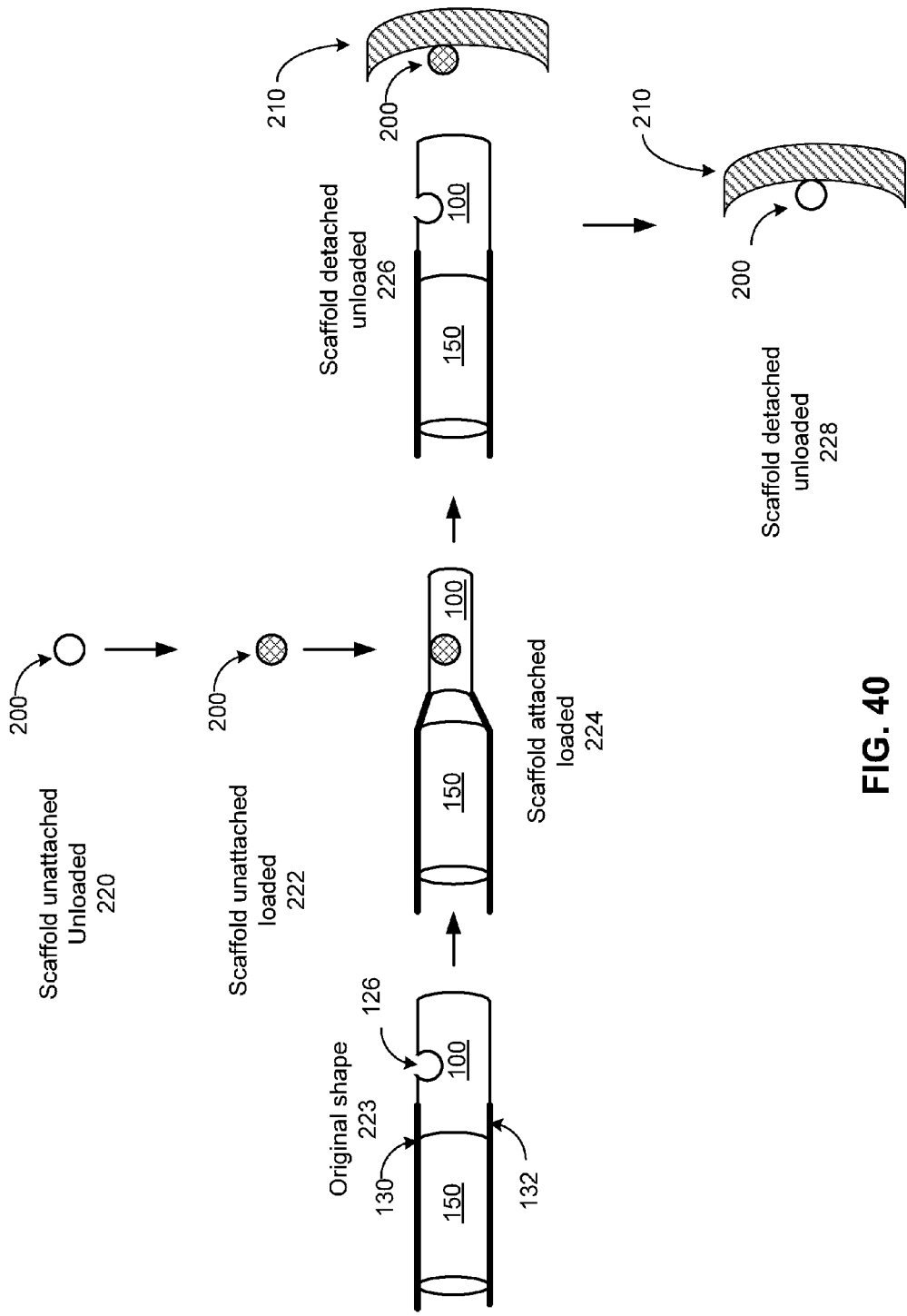
FIG. 40 is a pictorial diagram of a scaffold and catheter in accordance with an embodiment of the present invention.

FIG. 40 is a pictorial diagram of a scaffold and catheter in accordance with an embodiment of the present invention. In this embodiment, the scaffold 200 may be a shape-memory polymer or other biodegradable scaffold material delivered via a shape-memory polymer delivery device adhered to a delivery rod for targeted delivery, preferably through a catheter. The scaffold 200 can be placed in an area targeted for treatment while the delivery rod will retract the delivery device. The delivery device may grip the scaffold as shown, however or other gripping mechanisms may be possible. This scaffold 200 may be loaded with drugs, cells, or genetic material (as in the case of gene therapy), or other therapeutic substance. The loading of the scaffold 200 can be measured at a number of time points to allow for analysis.

In particular, an example is presented where a biodegradable scaffold 200 is loaded with therapeutic material and delivered via a shape memory catheterization device. In the state 220, the scaffold 200 is unattached and unloaded. The scaffold 200 can be exposed to the therapeutic source to begin loading. The loading data generator 302 is electrically coupled to the scaffold 200 to monitor the loading of the therapeutic material based on a change in impedance of the scaffold. When the loading is complete, as indicated or confirmed by the loading data 306, the load data generator 302 is detached.

In the state 222, the scaffold 200 is unattached and loaded. The scaffold 200 can be prepared for delivery or stored for later use. In the event of storage, the loading data 306 can be measured again prior to mounting on a delivery rod or other delivery device or after mounting but prior to catheterization to ensure that the scaffold 200 remains adequately loaded.

A shape memory member 100 is presented as a cylinder that is attached to a catheterization delivery rod 150 and is presented in its original shape 223. The shape memory member 100 includes a spherical pocket 126 for holding the scaffold 200. In the state 224, the loaded scaffold is attached. In the configuration shown, the pocket 126 is packed with the scaffold to be deployed and is then deformed from its original shape into a catheterization shape via crimping a portion of the cylinder shown. As shown, the pocket 126 of the original shape 125 is closed in the catheterization shape to hold the scaffold for catheterization in a pocket 126 for deployment.

In state 226, the loaded scaffold is detached and delivered to a tissue site 210 in a patient. When the shape memory member 100 is heated during deployment and transforms into transformed shape that is substantially the original shape, subject to, for example, physical conformity to the tissue, such as the vein, artery or other tissue in which the shape memory device is deployed. The pocket 126 opens for release of the scaffold 200 to the tissue site 210. In the state 228, the scaffold unloads the therapeutic material at the tissue site 210 and can then biodegrade or otherwise remain or pass through the body without harm to the patient.

While not specifically shown, the transformation data generator 102 is coupled to the electrodes 130 and 132 to generate transformation data 106 that indicates the shape transformation of the shape memory member 100 as previously described.

The plurality of electrodes 130 and 132 can be formed of a biocompatible wire or foil such as gold or other biocompatible metal or metal alloy, a shape memory polymer with electrically conductive properties, such as a shape memory polymer that is surface doped with a conductive compound. In a further example the plurality of electrodes 130 and 132 can be formed a flexible conductive foam member or insert or other conductive member.

In embodiments where the shape memory member 100 includes a shape memory polymer, the shape memory polymer can also be doped with a drug, such as an anticoagulant to reducing clotting, or other drug. While a particular scaffold 200 is shown, other medical devices can similarly be deployed. Further, while the scaffold is shown with a spherical shape, other designs including a pyramid, a box or other shapes can likewise be implemented.

Figure 41:
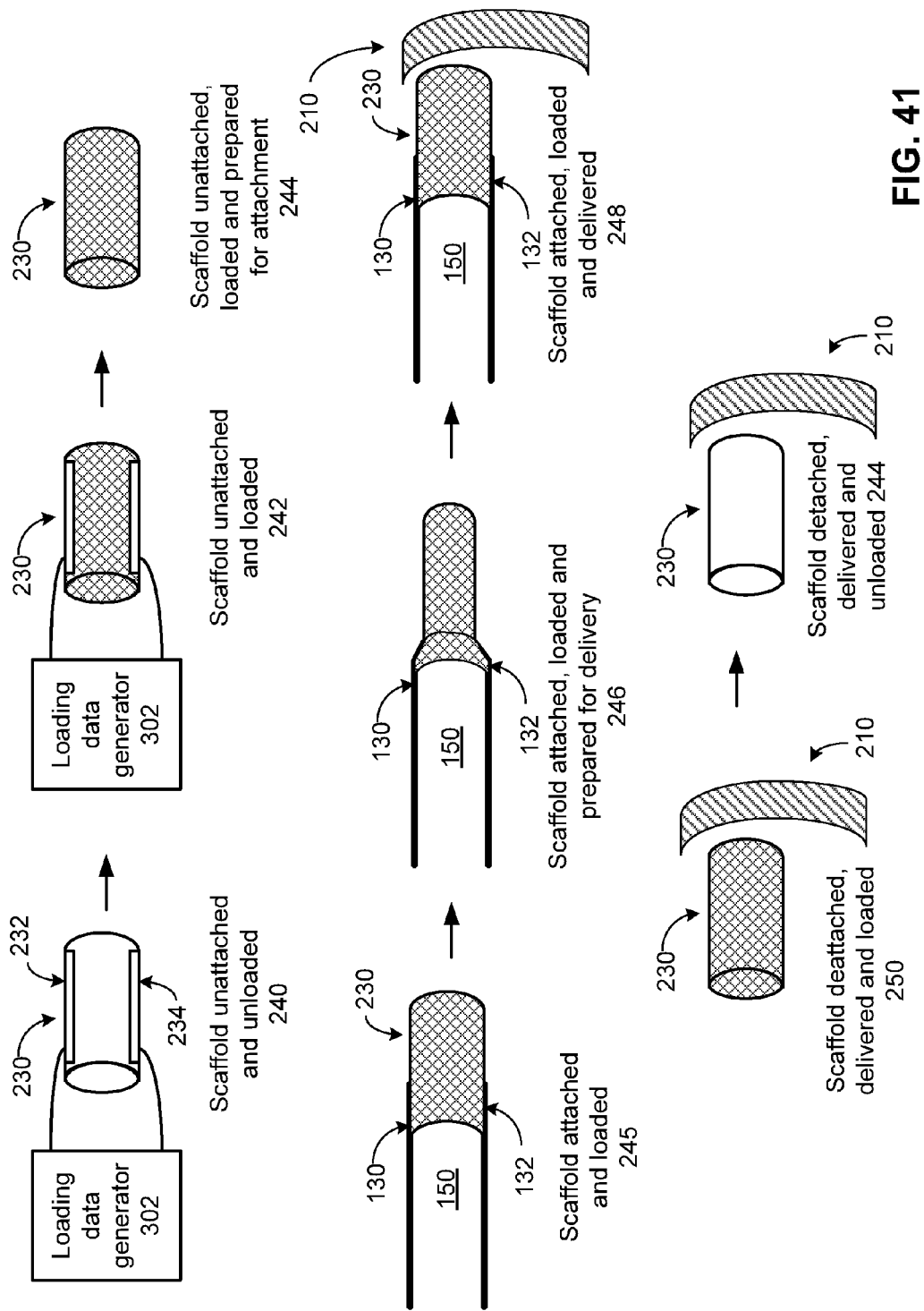
FIG. 41 is a pictorial diagram of a scaffold and catheter in accordance with an embodiment of the present invention.

FIG. 41 is a pictorial diagram of a scaffold and catheter in accordance with an embodiment of the present invention. In particular, an example is presented where a biodegradable scaffold 230, a further example of scaffold 200, is constructed of a shape memory material is loaded with therapeutic material and delivered via a catheterization device. In the state 240, a scaffold 230 is unattached and unloaded. The scaffold 230 can be exposed to the therapeutic source to begin loading. The loading data generator 302 is electrically coupled to the scaffold 230 to monitor the loading of the therapeutic material based on a change in impedance of the scaffold via the electrodes 232 and 234. In particular, the optional electrodes the electrodes 232 and 234 are formed of a metal foil adhered to the surface of the scaffold or other electrodes that are attached to the scaffold 230 to facilitate the connection to the loading data generator 302. While two electrodes are shown, a greater number can be employed, particularly in circumstances where the impedance of the scaffold is measured at a plurality of different points in the scaffold.

In the state 242, the scaffold 230 is unattached and loaded. When the loading is complete, as indicated or confirmed by the loading data 306, the load data generator 302 can be detached. The scaffold 230 can be prepared for delivery or stored for later use. In the event of storage, the loading data 306 can be measured again prior to mounting on a delivery rod or other delivery device or after mounting but prior to catheterization to ensure that the scaffold 230 remains adequately loaded.

In the state 244, the electrodes 232 and 234 are optionally removed from the scaffold 200 at some time prior to the attachment to the catheterization delivery rod 150. In an embodiment, the scaffold 230 is biodegradable and the electrodes 232 and 234 are formed of a non-biodegradable substance and can be removed prior to delivery. In other embodiments, the electrodes 232 and 234 are biodegradable or otherwise biocompatible such as a biocompatible foil, conductive ink, a biodegradable polymer member doped with carbon nanotubes or gold nanoparticles, a conductive foam member or insert or other biodegradable or biocompatible conductive element. In this case, the electrodes 230 and 232 can be included on the scaffold and/or not detached and further can be reused in connections to electrodes 130 and 132 of the delivery rod 150.

In the state 245, the loaded scaffold 230 is attached to the delivery rod 150. In the state 246, the scaffold 230 is then deformed from its original shape into a catheterization shape via crimping a portion of the cylinder shown. As shown, the electrodes 130 and 132 are crimped in place and provide a connection to the scaffold 230 for catheterization and delivery to a tissue site.

In state 248, the loaded scaffold is delivered to a tissue site 210 in a patient. When the scaffold 230 is heated during deployment and transforms into transformed shape that is substantially the original shape, subject to, for example, physical conformity to the tissue, such as the vein, artery or other tissue in which the shape memory device is ready to be released from the delivery rod 150. While not specifically shown, the transformation data generator 102 is coupled to the electrodes 130 and 132 to generate transformation data 106 that indicates the shape transformation of the scaffold 230 as previously described.

In state 250, the loaded scaffold 230 is released at the tissue site 210. In the state 252, the scaffold 230 unloads the therapeutic material at the tissue site 210 and can then biodegrade or otherwise remain or pass through the body without harm to the patient.

Figure 42:
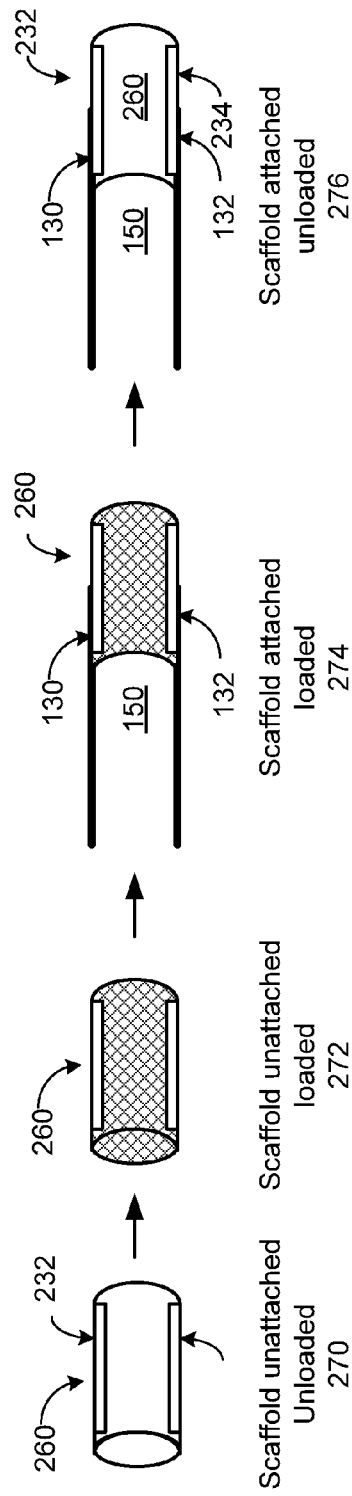
FIG. 42 is a pictorial diagram of a scaffold and catheter in accordance with an embodiment of the present invention.

FIG. 42 is a pictorial diagram of a scaffold and catheter in accordance with an embodiment of the present invention. In particular, an example is presented where a scaffold 260, a further example of scaffold 200, is loaded with therapeutic material and delivered via a catheterization device that monitors the unloading of the scaffold 260 and removes the scaffold from the body of the patent when unloading is complete.

In the state 270, a scaffold 260 is unattached and unloaded. The scaffold 260 can be exposed to the therapeutic source to begin loading. The loading data generator 302 (not shown) is electrically coupled to the scaffold 260 to monitor the loading of the therapeutic material based on a change in impedance of the scaffold via the electrodes 232 and 234. In particular, the optional electrodes the electrodes 232 and 234 are formed of a metal foil adhered to the surface of the scaffold or other electrodes that are attached to the scaffold 260 to facilitate the connection to the loading data generator 302. While two electrodes are shown, a greater number can be employed, particularly in circumstances where the impedance of the scaffold is measured at a plurality of different points in the scaffold.

In the state 272, the scaffold 260 is unattached and loaded. When the loading is complete, as indicated or confirmed by the loading data 306, the load data generator 302 can be detached. The scaffold 260 can be prepared for delivery or stored for later use. In the event of storage, the loading data 306 can be measured again prior to mounting on a delivery rod or other delivery device or after mounting but prior to catheterization to ensure that the scaffold 260 remains adequately loaded.

In the state 272, the electrodes 232 and 234 are optionally removed from the scaffold 200 at some time prior to the attachment to the catheterization delivery rod 150. In the embodiment shown, the electrodes 230 and 232 are reused in connections to electrodes 130 and 132 of the delivery rod 150. In the state 274, the loaded scaffold 260 is attached to the delivery rod 150 and is delivered to a tissue site in a patient. While not specifically shown, the loading data generator 302 is coupled to the electrodes 130 and 132 to generate further loading data 306 that indicates the unloading of the therapeutic material from the scaffold 260 as previously described. In the state 276, the scaffold 260 unloads the therapeutic material at the tissue site. When the loading data 306 indicates the unloading is complete, the scaffold 260 can be removed from the body of the patient by retracting the delivery rod 150 via the catheter.

Figure 43:
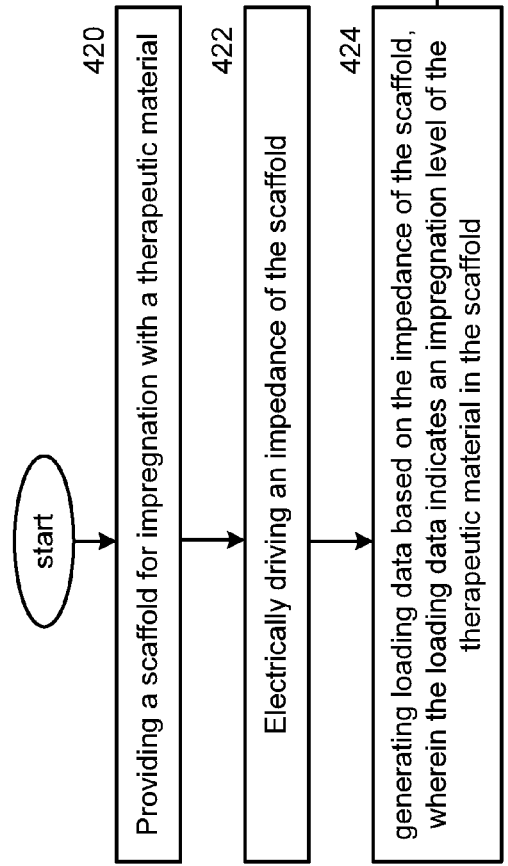
FIG. 43 is a flowchart representation of an embodiment of a method in accordance with the present invention.

FIG. 43 is a flowchart representation of an embodiment of a method in accordance with the present invention. In particular a method is presented for use in conjunction with one or more functions and features presented in conjunction with FIGS. 1-42. Step 420 includes providing a scaffold for impregnation with a therapeutic material. Step 422 includes electrically driving an impedance of the scaffold. Step 424 includes generating loading data based on the impedance of the scaffold, wherein the loading data indicates an amount of impregnation of the therapeutic material in the scaffold.

In an embodiment, the loading data provides an indication when the impregnation of the therapeutic material is complete. The scaffold can be coupled to a delivery rod for the delivery in the patient via catheterization. The driving circuit can be coupled to the scaffold via a plurality of electrodes. The loading data can indicate a first loading measurement prior to the catheterization, a second loading measurement when the scaffold is delivered in the patient, and a third loading measurement when the scaffold is delivered in the patient, wherein the third loading measurement indicates the therapeutic material is unloaded from the scaffold.

FIG. 44 is a flowchart representation of an embodiment of a method in accordance with the present invention. In particular a method is presented for use in conjunction with one or more functions and features presented in conjunction with FIGS. 1-43. Step 400 includes endovascular insertion of a scaffold via a catheter, wherein the scaffold is impregnated with a therapeutic material. Step 402 includes driving a circuit that includes an impedance of the scaffold. Step 404 includes generating loading data based on the impedance of the scaffold, wherein the loading data indicates a delivery of the therapeutic material from the scaffold. Step 406 includes determining that the delivery of the therapeutic material is complete based on the loading data.

FIG. 45 is a flowchart representation of an embodiment of a method in accordance with the present invention. In particular a method is presented for use in conjunction with one or more functions and features presented in conjunction with FIGS. 1-44. Step 410 includes impregnating a scaffold with a therapeutic material. Step 412 includes driving a circuit that includes an impedance of the scaffold. Step 414 includes generating loading data based on the impedance of the scaffold, wherein the loading data indicates an amount of impregnation of the therapeutic material in the scaffold. Step 416 includes determining that the impregnation of the therapeutic material is complete based on the loading data.

FIG. 46 is a schematic block diagram of an embodiment of driver circuit and detection circuit in accordance with the present invention. In particular a driver circuit 112 and detector circuit 114 are shown for use in conjunction with a transformation data generator, such as transformation data generator 102.

While transformation data generator 102 has been primarily discussed in terms of the measurement of strain, resistance, capacitance, inductance or impedance other properties can be used in addition to or in place of strain, resistance, capacitance, inductance or impedance. In an embodiment, transformation data generator 102 include a driver 500 and detector 502 coupled to the shape memory member 100 that measure a spectral conductance, reflection, transmission or absorption of a light wave that is transmitted through the shape memory member 100. In a further example, transformation data generator 102 can include a driver 500 and detector 502 coupled to the shape memory member 100 that measure a spectral conductance, reflection, transmission or absorption of an RF wave such as a far-field or near field millimeter wave signal wave that is transmitted through the shape memory member 100. While the driver 500 and detector 502 are shown as being on opposing sides of shape memory member 100, other configurations are likewise possible. It should be noted that this alternative mode of operation of transformation data generator 102 can be used in place of any of the prior embodiments discussed in conjunction with FIGS. 1-30 and 32.

In the operation of the transformation data generator 102, the driver 500 of driver circuit 112 includes an RF transmitter having an antenna or coil or a light emitting element such as a light emitting diode, a laser diode or other miniature light source that produces an RF or lightwave that is transmitted into the shape memory member 100. The transformation data generator 102 also includes a detection circuit 114 having a detector 502 that includes an antenna or coil and an RF receiver or lightwave detector such as a photo detector, photocell or detector that is coupled to a processor or other circuit included in the detection circuit for generating transformation data 106. The transformation data 106 indicates a shape transformation of the shape memory member 100 device from the catheterization shape to the transformed shape, based on changes in spectral conductance, reflection, transmission or absorption of the RF signal or lightwave driven to the shape memory member 100 by driver 500 and detected via detector 502. In an embodiment of the present invention the transformation data 106 can be displayed or otherwise used to provide visual, audible or tactile feedback to the users of a shape memory catheterization device 98 that the shape memory member 100 has reached its transformation shape.

FIG. 47 is a schematic block diagram of an embodiment of driver circuit and detection circuit in accordance with the present invention. In particular, a driver circuit 312 and detector circuit 314 are shown for use in conjunction with a loading data generator, such as loading data generator 302.

As previously discussed, loading data generator 302 can measure other properties in addition to or in place of resistance, capacitance, inductance or impedance. For example, loading data generator 302 can include a driver 500 and detector 502 coupled to the scaffold 200 or 230 that measure a spectral conductance, reflection, transmission or absorption of a light wave or RF wave that is transmitted into or through the scaffold 200 or 230. While the driver 500 and detector 502 are shown as being on opposing sides of scaffold 200 or 230, other configurations are likewise possible. It should be noted that this alternative mode of operation of loading data generator 302 can be used in place of any of the prior embodiments discussed in conjunction with FIGS. 31 and 33-45.

In the operation of the loading data generator 302, the driver 500 of driver circuit 312 includes an RF transmitter having an antenna or coil or a light emitting element such as a light emitting diode, a laser diode or other miniature light source that produces an RF or lightwave that is transmitted into the scaffold 200 or 230. The loading data generator 302 also includes a detection circuit 314 having a detector 502 that includes an antenna or coil and an RF receiver or lightwave detector such as a photo detector, photocell or detector that is coupled to a processor or other circuit included in the detection circuit for generating loading data 306. The loading data generator 306 interacts with the scaffold 200 via measurements to monitor the loading and unloading of the therapeutic material from the scaffold 200. In these further examples, loading data 306 can be generated based on loading profiles that present reflection, conductance, transmission or absorption of either light or RF waves as a function of time as the concentration of the therapeutic material increases during loading and/or unloading. In an embodiment of the present invention the loading data 306 can be displayed or otherwise used to provide visual, audible or tactile feedback to the users of a scaffold 200 or 230 that the scaffold 200 or 230 has been loaded or unloaded, partially loaded, loading or unloading has begun, is at a particular point on a loading or unloading profile, etc.

FIG. 48 is a schematic block diagram of an embodiment of a system for monitoring a scaffold 200' in accordance with the present invention. In particular, a scaffold 200' is presented this is similar to scaffold 200 discussed in conjunction with FIGS. 31 and 33 except that a loading data generator 302', similar to loading data generator 302 is attached to or incorporated in the scaffold 200' and communicates loading data 306 wirelessly with a wireless loading data receiver 510. Like scaffold 200, scaffold 200' can be delivered via a scaffold catheterization device 298 that includes catheter delivery rod 150, such as a push rod or other delivery mechanism. The loading data generator 302' can be coupled to the scaffold 200' to monitor the loading of the therapeutic material to the scaffold before delivery. In this embodiment, the loading data generator 302' is also capable of monitoring the unloading of the therapeutic material from the scaffold 200' after delivery in the patient and further after the scaffold 200' is detached from the catheter delivery rod 150.

The wireless loading data receiver receives the loading data 306 from the loading data generator 302'. The loading data 306 can be analyzed to track an unloading profile of the therapeutic material and further can provide an indication that the therapeutic material is adequately unloaded, i.e. that the desired amount of therapeutic material has been delivered by the scaffold to the patient in proximity to the site of the delivery.

Figure 49:
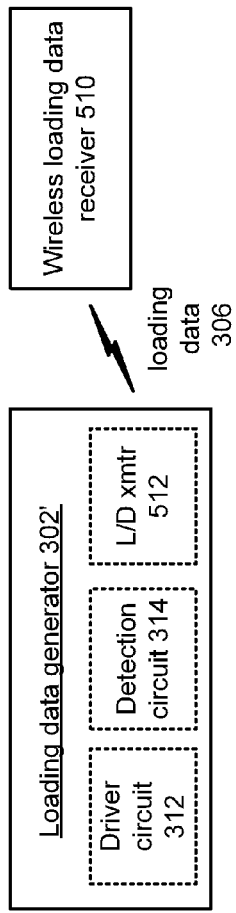
FIG. 49 is a schematic block diagram of an embodiment of a loading data generator in accordance with the present invention.

FIG. 49 is a schematic block diagram of an embodiment of a loading data generator in accordance with the present invention. A loading data generator 302' is shown that provides many of the functions and features described in conjunction with loading data generator 302. In particular, loading data generator 302' includes a driving circuit 312 that, for example, is electrically coupled to drive an impedance of the scaffold 200'. In this case, the detection circuit 314 generates loading data 306 based on the impedance of the scaffold 200', such as a capacitance, resistance, inductance or some combination thereof. The loading data 306 uses the impedance measurement to indicate an amount of impregnation of the therapeutic material in the scaffold 200, such as via a loading profile, an unloading profile or other function of the impedance of the scaffold 200.

Like loading data generator 302, the loading data generator 302' can measure other properties in addition to or in place of impedance. For example, loading data generator 302' can include a driver and detector coupled to the scaffold 200' that measure a spectral conductance, transmission or absorption of a light wave that is transmitted through the scaffold 200'. In a further example, loading data generator 302' can include a driver and detector coupled to the scaffold 200' that measure a spectral conductance, transmission or absorption of a millimeter wave or other RF signal transmitted through the scaffold 200'. In pertinent part, loading data generator 302' interacts with the scaffold 200' via measurements to monitor the loading and unloading of the therapeutic material from the scaffold 200'. The detection circuit 314 can include a processor or other processing device or circuit.

In addition, loading data generator 302' includes a loading data transmitter 512 that communicates with the loading data 306 with the wireless loading data receiver 510. In an embodiment, the loading data transmitter 512 and wireless loading data receiver 510 can each be part of corresponding transceivers that operate in conjunction with a communication standard such as 802.11, Bluetooth, ZigBee, ultra-wideband, RF identification (RFID), Wimax or other standard short or medium range communication protocol, or other protocol. In one example of operation, the loading data generator 302' operates in a similar fashion to a passive RFID tag and wireless loading data receiver 510 operates as an RFID reader to provide an energy signal to power the loading data generator 302'.

In an embodiment, the loading data generator 302' is constructed of a biodegradable circuit capable of in vivo operation in conjunction with a delivery system for tissue engineering and/or drug delivery. In an embodiment, all components of the circuit are made of biodegradable materials. The circuit can be built upon a biodegradable substrate such as silk, fabric, paper, caramelized glucose and/or polymers such as poly(L-lactide-co-glycolide) and thermoplastic polyesters. The circuit itself can be printed onto any of these substrates using a biocompatible, conductive ink. The substrates with associated circuits are connected via a biodegradable conductive wire, for example cotton fiber impregnated with carbon nanotubes or gold nanoparticles or a biodegradable polymer fiber doped with carbon nanotubes or gold nanoparticles. In another embodiment this wire may be composed of iron, magnesium, or alloys of the two metals, which are both conductive and biodegradable.

In another embodiment, several individual circuits are made of a biocompatible material small enough to be eluted from the body without biodegradation. For example, circuits could be printed on gold nanoparticles, which are commercially available through Sigma Aldrich. These nanoparticles would then be connected with a wire similar as discussed above. In either embodiment, a biodegradable battery may power the circuit. This battery may be single use or may be recharged via remote methods, such as the use of radio frequency charging. This would allow for non-invasive charging of the battery for prolonged power to the circuit.

Figure 50:
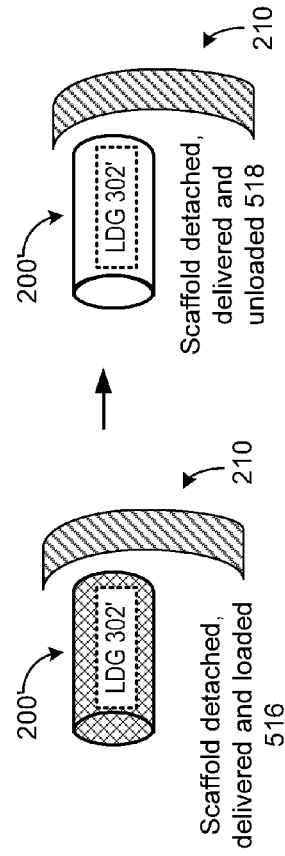
FIG. 50 is a pictorial diagram of a scaffold in accordance with an embodiment of the present invention.

FIG. 50 is a pictorial diagram of a scaffold in accordance with an embodiment of the present invention. In particular, an embodiment is shown that is similar to the scaffold delivery described in conjunction with FIG. 41. In this embodiment, scaffold 200' is delivered in place of scaffold 230. In state 516, the loaded scaffold 200' is delivered and detached at the tissue site 210. In the state 518, the scaffold 200' unloads the therapeutic material at the tissue site 210 and can then biodegrade or otherwise remain or pass through the body without harm to the patient.

To preserve the monitoring of loading data 306, the loading data generator 302' is capable of biodegradation at slower rate than the unloading and biodegradation of the scaffold 200'. In this fashion, the loading data generator 302' can continue to operate until the unloading and/or biodegradation of the scaffold 200' is completed. To achieve this, the circuit can itself be biodegradable at a slower rate or can be encapsulated in a second material such as a biodegradable plastic or film with a slower degradation rate than the scaffold 200' used for the delivery system to preserve monitoring functionality until the scaffold system has adequately unloaded and/or degraded.

Figure 51:
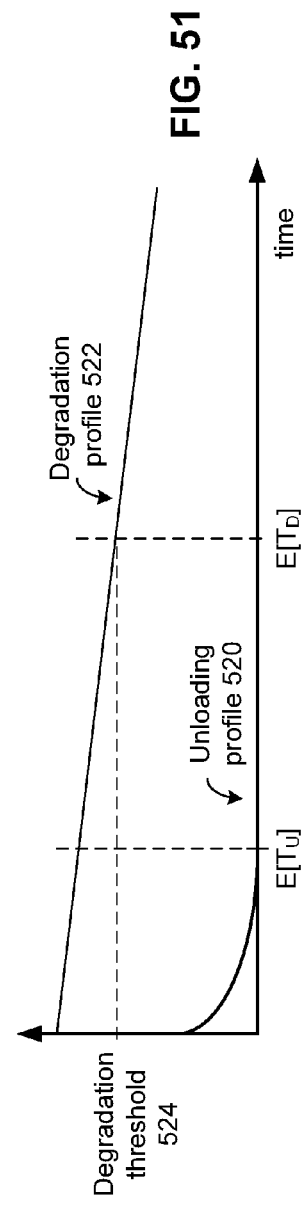
FIG. 51 is a graphical representation of an unloading profile in accordance with an embodiment the present invention.

FIG. 51 is a graphical representation of an unloading profile in accordance with an embodiment the present invention. In particular, an unloading profile 520 is shown as a function of concentration of therapeutic material loaded in a scaffold, such as scaffold 200', as a function of time. As shown the concentration of therapeutic material falls as the scaffold 200' is unloaded until an expected unloading time $E[T_U]$ is reached. On the same graph, a degradation profile 522 is presented that represents the amount of biodegradation of the loading data generator 302'. In particular, the loading data generator 302' slowly degrades until a degradation threshold 524 is reached at an expected degradation time $E[T_D]$. The degradation threshold 524 can be chosen to correspond to a point of first failure—i.e. the time where the operation of the loading data generator 302' would cease due to biodegradation.

For example, the an expected degradation time $E[T_D]$ represents a mean time to failure of the loading data generator 302'. As shown, $E[T_D]$ exceeds the value $E[T_U]$ to ensure that the loading data generator 302' is still in operation at the time that unloading is expected to be complete in order to generate loading data 306 to indicate this event. It should be noted that the loading data generator 302' can be designed so that $E[T_D]$ exceeds the value $E[T_U]$ by a sufficient margin to provide confidence that loading data generator 302' is operating properly at $E[T_U]$. In an embodiment, the margin is selected to provide a statistical confidence, such as 95% confidence, 99% confidence or some greater or lesser confidence level that failure of the loading data generator 302' does not occur before unloading of the scaffold 200' is complete.

Figure 52:
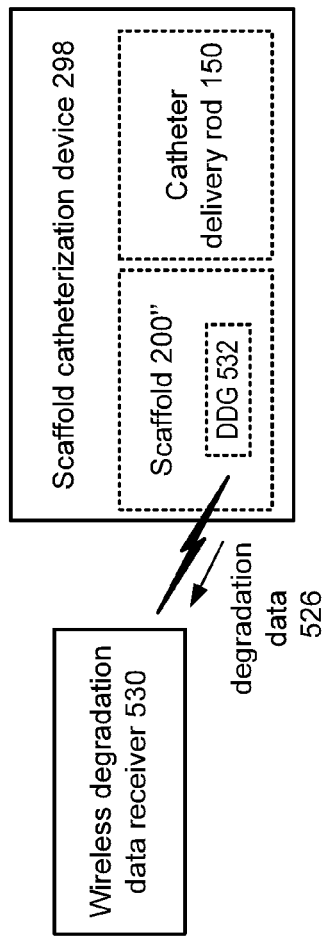
FIG. 52 is a schematic block diagram of an embodiment of a system for monitoring a scaffold in accordance with the present invention.

FIG. 52 is a schematic block diagram of an embodiment of a system for monitoring a scaffold 200" in accordance with the present invention. In particular, a scaffold 200" is presented this is similar to scaffold 200' discussed in conjunction with FIGS. 48-51 except that a degradation data generator 532, similar to loading data generator 302' is attached to or incorporated in the scaffold 200" and communicates degradation data 526 wirelessly with a wireless degradation data receiver 530. Like scaffold 200', scaffold 200" can be delivered via a scaffold catheterization device 298 that includes catheter delivery rod 150, such as a push rod or other delivery mechanism. The degradation data generator 532 can be coupled to the scaffold 200" to monitor the degradation of the scaffold after delivery.

The wireless degradation data receiver 530 receives the degradation data 526 from the degradation data generator 532. The degradation data 526 can be analyzed to track a degradation profile of the scaffold and further can provide an indication that the scaffold is adequately degraded, i.e. that sufficient degradation has occurred to permit any remaining portions of the scaffold to pass through the body or otherwise remain without harm to the patient.

Figure 53:
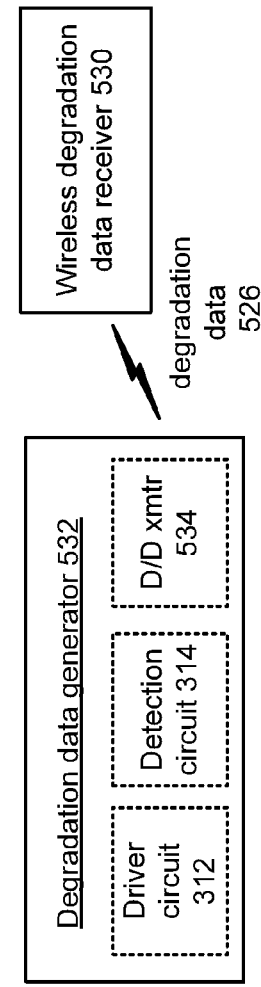
FIG. 53 is a schematic block diagram of an embodiment of a degradation data generator in accordance with the present invention.

FIG. 53 is a schematic block diagram of an embodiment of a degradation data generator in accordance with the present invention. A degradation data generator 532 is shown that operates in a similar fashion to loading data generator 302'. In particular, degradation data generator 532 includes a driving circuit 312 that, for example, is electrically coupled to drive an impedance of the scaffold 200". In this case, the detection circuit 314 generates degradation data 526 based on the impedance of the scaffold 200", such as a capacitance, resistance, inductance or some combination thereof. The degradation data generator 532 uses the impedance measurement to indicate an amount of degradation of the scaffold 200", such as via a degradation profile, or other function of the impedance of the scaffold 200".

Like loading data generator 302', the degradation data generator 532 can measure other properties in addition to or in place of impedance. For example, degradation data generator 532 can include a driver and detector coupled to the scaffold 200" that measure a spectral conductance, transmission or absorption of a light wave that is transmitted through the scaffold 200". In a further example, degradation data generator 532 can include a driver and detector coupled to the scaffold 200" that measure a spectral conductance, transmission or absorption of a millimeter wave or other RF signal transmitted through the scaffold 200". In pertinent part, degradation data generator 532 interacts with the scaffold 200" via measurements to monitor the degradation of the scaffold 200". The detection circuit 314 can include a processor or other processing device or circuit.

In addition, degradation data generator 532 includes a degradation data transmitter 534 that communicates with the degradation data 526 with the wireless degradation data receiver 530. In an embodiment, the degradation data transmitter 534 and wireless degradation data receiver 530 can each be part of corresponding transceivers that operate in conjunction with a communication standard such as 802.11, Bluetooth, ZigBee, ultra-wideband, RF identification (RFID), Wimax or other standard short or medium range communication protocol, or other protocol. In one example of operation, the degradation data generator 532 operates in a similar fashion to a passive RFID tag and wireless degradation data receiver 530 operates as an RFID reader to provide an energy signal to power the degradation data generator 532.

In an embodiment, the degradation data generator 532 is constructed of a biodegradable circuit capable of in vivo operation in conjunction with a delivery systems for tissue engineering and drug delivery. In an embodiment, all components of the circuit are made of biodegradable materials. The circuit can be built upon a biodegradable substrate such as silk, fabric, paper, caramelized glucose and/or polymers such as poly(L-lactide-co-glycolide) and thermoplastic polyesters. The circuit itself can be printed onto any of these substrates using a biocompatible, conductive ink. The substrates with associated circuits are connected via a biodegradable conductive wire, for example cotton fiber impregnated with carbon nanotubes or gold nanoparticles or a biodegradable polymer fiber doped with carbon nanotubes or gold nanoparticles. In another embodiment this wire may be composed of iron, magnesium, or alloys of the two metals, which are both conductive and biodegradable.

In another embodiment, several individual circuits are made of a biocompatible material small enough to be eluted from the body without biodegradation. For example, circuits could be printed on gold nanoparticles, which are commercially available through Sigma Aldrich. These nanoparticles would then be connected with a wire similar as discussed above. In either embodiment, a biodegradable battery may power the circuit. This battery may be single use or may be recharged via remote methods, such as the use of radio frequency charging. This would allow for non-invasive charging of the battery for prolonged power to the circuit.

Figure 54:
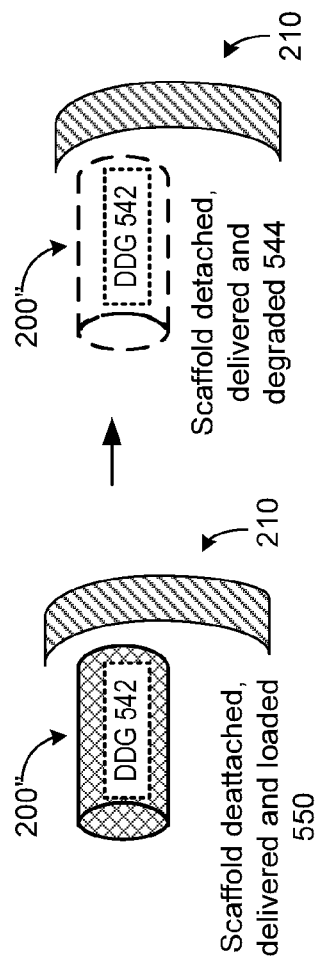
FIG. 54 is a pictorial diagram of a scaffold in accordance with an embodiment of the present invention.

FIG. 54 is a pictorial diagram of a scaffold in accordance with an embodiment of the present invention. In particular, an embodiment is shown that is similar to the scaffold delivery described in conjunction with FIG. 41. In this embodiment, scaffold 200" is delivered in place of scaffold 230. In state 550, the loaded scaffold 200" is delivered and detached at the tissue site 210. In the state 544, the scaffold 200" unloads the therapeutic material at the tissue site 210 and further, has biodegraded.

To preserve the monitoring of degradation data 306, the degradation data generator 532 is capable of biodegradation at slower rate than the unloading and biodegradation of the scaffold 200". In this fashion, the degradation data generator 532 can continue to operate until the unloading and biodegradation of the scaffold 200" is completed. To achieve this, the circuit can itself be biodegradable at a slower rate or can be encapsulated in a second material with a slower degradation rate than the scaffold 200" used for the delivery system to preserve monitoring functionality until the scaffold system has adequately unloaded and/or degraded.

Figure 55:
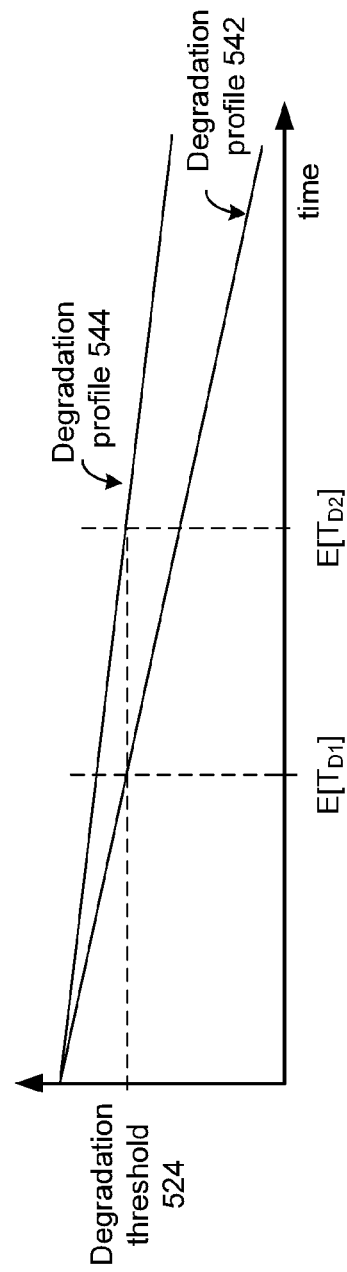
FIG. 55 is a graphical representation of degradation profiles in accordance with an embodiment the present invention.

FIG. 55 is a graphical representation of a degradation profile in accordance with an embodiment the present invention. In particular, a degradation profile 542 is shown for a scaffold, such as scaffold 200", as a function of time. As shown, the scaffold 200" slowly degrades until a degradation threshold 524 is reached at an expected degradation time $E[T_{D1}]$. The degradation threshold is chosen to correspond to a point where the operation of the scaffold 200' is sufficiently degraded to allow the remaining portions of the scaffold 200' to pass through the body of the patient or remain without harm. On the same graph, a degradation profile 544 is presented that represents the amount of biodegradation of the degradation data generator 532. In particular, the degradation data generator 532 slowly degrades until a degradation threshold 524 is reached at an expected degradation time $E[T_{D1}]$. The degradation threshold 524 is chosen to correspond to a point where the operation of the degradation data generator 532 would cease due to biodegradation. While the same degradation threshold 524 is shown for both the degradation data generator 532 and the scaffold 200", different degradation thresholds can be used. In an embodiment, while the degradation threshold for the degradation data generator 532 is chosen to represent first failure, a lower degradation threshold for the scaffold 200" can be used to represented that the scaffold has substantially degraded, i.e. that sufficient degradation has occurred to allow the remaining portions of the scaffold 200' to pass through the body of the patient or remain without harm.

For example, the an expected degradation time $E[T_{D2}]$ represents a mean time to failure of the degradation data generator 532. As shown, $E[T_{D2}]$ exceeds the value $E[T_{D1}]$ to ensure that the degradation data generator 532 is still in operation at the time that degradation of scaffold 200" is expected to be complete in order to generate degradation data 526 to indicate this event. It should be noted that the degradation data generator 532 can be designed so that $E[T_{D2}]$ exceeds the value $E[T_{D1}]$ by a sufficient margin to provide confidence that degradation data generator 532 is operating properly at $E[T_{D1}]$. In an embodiment, the margin is selected to provide a statistical confidence, such as 95% confidence, 99% confidence or some greater or lesser confidence level that failure of the degradation data generator 532 does not occur before degradation of the scaffold 200" is complete.

FIG. 56 is a flowchart representation of an embodiment of a method in accordance with the present invention. In particular a method is presented for use in conjunction with one or more functions and features presented in conjunction with FIGS. 1-55. Step 600 includes endovascular insertion of a biodegradable scaffold via a catheter, wherein the scaffold is impregnated with a therapeutic material. Step 602 includes electrically driving a circuit that includes an impedance of the scaffold via a biodegradable driving circuit. Step 604 includes generating loading data based on the impedance of the scaffold via a biodegradable detection circuit, wherein the loading data indicates unloading of the therapeutic material from the scaffold. Step 606 includes wirelessly transmitting the loading data to a wireless loading data receiver via a biodegradable wireless transmitter of the scaffold.

FIG. 57 is a flowchart representation of an embodiment of a method in accordance with the present invention. In particular a method is presented for use in conjunction with one or more functions and features presented in conjunction with FIGS. 1-56. Step 610 includes endovascular insertion of a biodegradable scaffold via a catheter, wherein the scaffold is impregnated with a therapeutic material. Step 612 includes driving the scaffold via a biodegradable driving circuit that generates an RF signal or lightwave. Step 614 includes generating loading via a biodegradable detection circuit of the scaffold, wherein the loading data indicates unloading of the therapeutic material from the scaffold. Step 616 includes wirelessly transmitting the loading data to a wireless loading data receiver via a biodegradable wireless transmitter of the scaffold.

FIG. 58 is a flowchart representation of an embodiment of a method in accordance with the present invention. In particular a method is presented for use in conjunction with one or more functions and features presented in conjunction with FIGS. 1-57. Step 620 includes endovascular insertion of a biodegradable scaffold via a catheter. Step 622 includes electrically driving a circuit that includes an impedance of the scaffold via a biodegradable driving circuit. Step 624 includes generating degradation data based on the impedance of the scaffold via a biodegradable detection circuit, wherein the degradation data indicates biodegradation of the scaffold. Step 626 includes wirelessly transmitting the degradation data to a wireless loading data receiver via a biodegradable wireless transmitter of the scaffold.

FIG. 59 is a flowchart representation of an embodiment of a method in accordance with the present invention. In particular a method is presented for use in conjunction with one or more functions and features presented in conjunction with FIGS. 1-58. Step 630 includes endovascular insertion of a biodegradable scaffold via a catheter. Step 632 includes driving the scaffold via a biodegradable driving circuit that generates an RF signal or lightwave. Step 634 includes generating degradation data via a biodegradable detection circuit of the scaffold, wherein the degradation data indicates biodegradation of the scaffold. Step 636 includes wirelessly transmitting the degradation data to a wireless loading data receiver via a biodegradable wireless transmitter of the scaffold.

While the foregoing description has focused on heat induced shape memory transformation, transformation can be actuated via other stimuli. For example, shape transformations can be actuated via exposure to liquids such as water or other chemicals, by solution pH, solvent composition, electrical and magnetic fields, sonic or ultrasonic waves, ultraviolet, visible or other light or other actuation modes. The various embodiments described herein can be modified to any of these additional shape memory transformation modes. In these cases, the various temperature thresholds corresponding to the state transitions of a shape memory element are implemented instead by stimulation thresholds corresponding to the particular transformation stimulus or stimuli employed. Further, while a single stimulus has been discussed for implementing the transition between the various states of a shape memory element, multiple different stimuli can be employed.

As may be used herein, the terms "substantially" and "adequately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments of an invention have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

The one or more embodiments are used herein to illustrate one or more aspects, one or more features, one or more concepts, and/or one or more examples of the invention. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments. A module includes a processing module, a processor, a functional block, hardware, and/or memory that stores operational instructions for performing one or more functions as may be described herein. Note that, if the module is implemented via hardware, the hardware may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure of an invention is not limited by the particular examples disclosed herein and expressly incorporates these other combinations.

What is claimed is:

1. A degradation data generator comprising:
a scaffold for delivery within a patient;
a driving circuit electrically coupled to drive an impedance of the scaffold, wherein the scaffold is coupled to a delivery rod for the delivery in the patient via catheterization and wherein the driving circuit is coupled to the scaffold via a plurality of electrodes;
a detection circuit, coupled to the driving circuit, that includes at least one portion of the scaffold that forms a passive circuit element of the detection circuit, wherein the detection circuit generates degradation data based on an impedance of the passive circuit element, and wherein the degradation data indicates an amount of biodegradation of the scaffold; and
a wireless transmitter, coupled to transmit the degradation data to a wireless degradation data receiver, while the scaffold is within the patient.

2. The degradation data generator of claim 1 wherein the degradation data provides an indication when the biodegradation of the scaffold is complete.

3. The degradation data generator of claim 1 wherein the degradation data indicates a first degradation measurement when the scaffold is delivered in the patient.

4. The degradation data generator of claim 3 wherein the degradation data indicates a second degradation measurement when the scaffold is delivered in the patient, wherein the second degradation measurement indicates the biodegradation of the scaffold is complete.

5. The degradation data generator of claim 1 wherein the detection circuit measures a capacitance of the scaffold.

6. The degradation data generator of claim 1 wherein the detection circuit monitors a degradation profile of the scaffold.

7. The degradation data generator of claim 1 wherein the degradation data generator is biodegradable.

8. The degradation data generator of claim 7 wherein the degradation data generator is characterized by a first degradation profile and the scaffold is characterized by a second degradation profile that is different from the first degradation profile.

9. The degradation data generator of claim 7 wherein the degradation data generator has a first expected degradation time that is greater than a second expected degradation time associated with the scaffold.

10. The degradation data generator of claim 1 wherein the impedance of the scaffold includes a first impedance at a first location of the scaffold and a second impedance at a second location of the scaffold.

11. The degradation data generator of claim 1, wherein the scaffold is a shape memory polymer.

* * * * *